United States Patent
Suh et al.

(10) Patent No.: US 10,486,971 B2
(45) Date of Patent: Nov. 26, 2019

(54) SCROLL COMPOSITE HAVING AMPHIPHILIC SUBSTANCE INSIDE AND METHOD FOR PREPARATION OF THE SAME

(71) Applicant: INDUSTRY-UNIVERSITY COOPERATION FOUNDATION HANYANG UNIVERSITY, Seoul (KR)

(72) Inventors: Donghack Suh, Seongnam-si (KR); Dayoung Hwang, Seoul (KR)

(73) Assignee: INDUSTRY-UNIVERSITY COOPERATION FOUNDATION HANYANG UNIVERSITY, Seoul (KR)

( * ) Notice: Subject to any disclaimer, the term of this patent is extended or adjusted under 35 U.S.C. 154(b) by 150 days.

(21) Appl. No.: 15/117,575

(22) PCT Filed: Mar. 2, 2015

(86) PCT No.: PCT/KR2015/001976
§ 371 (c)(1),
(2) Date: Aug. 9, 2016

(87) PCT Pub. No.: WO2015/133776
PCT Pub. Date: Sep. 11, 2015

(65) Prior Publication Data
US 2016/0355401 A1   Dec. 8, 2016

(30) Foreign Application Priority Data

Mar. 4, 2014   (KR) .................. 10-2014-0025413
Feb. 25, 2015  (KR) .................. 10-2015-0026298

(51) Int. Cl.
*C01B 32/18*    (2017.01)
*C01B 21/064*   (2006.01)
(Continued)

(52) U.S. Cl.
CPC .......... *C01B 32/18* (2017.08); *C01B 21/0648* (2013.01); *C01B 32/194* (2017.08);
(Continued)

(58) Field of Classification Search
CPC ..................................................... C01B 32/18
See application file for complete search history.

(56) References Cited

U.S. PATENT DOCUMENTS

| | | | |
|---|---|---|---|
| 2008/0170982 A1* | 7/2008 | Zhang | B82Y 10/00 |
| | | | 423/447.3 |
| 2010/0009165 A1* | 1/2010 | Patel | C09D 7/70 |
| | | | 428/323 |

(Continued)

FOREIGN PATENT DOCUMENTS

| | | |
|---|---|---|
| CN | 102674336 A | 9/2012 |
| KR | 20100025615 A | 3/2010 |

OTHER PUBLICATIONS

Braga et al., Nanoletters 2004, vol. 4(5), 881-884 (Year: 2004).*
(Continued)

*Primary Examiner* — Liam J Heincer

(57) ABSTRACT

Provided are a scroll preparing method using a two-dimensional material and a scroll prepared thereby. The scroll preparing method comprises preparing a two-dimensional material. The two-dimensional material is scrolled by providing an amphiphilic substance having a hydrophilic portion and a hydrophobic portion on the two-dimensional material. As a result, a scroll composite including the amphiphilic substance disposed inside a scroll structure is formed.

29 Claims, 12 Drawing Sheets

(51) Int. Cl.
| | |
|---|---|
| C01G 39/06 | (2006.01) |
| C01G 41/00 | (2006.01) |
| C01G 41/02 | (2006.01) |
| C01G 45/02 | (2006.01) |
| C01B 32/23 | (2017.01) |
| C01B 32/194 | (2017.01) |
| C07J 41/00 | (2006.01) |
| C07J 9/00 | (2006.01) |
| C07J 31/00 | (2006.01) |

(52) U.S. Cl.
 CPC .............. *C01B 32/23* (2017.08); *C01G 39/06* (2013.01); *C01G 41/00* (2013.01); *C01G 41/02* (2013.01); *C01G 45/02* (2013.01); *C01P 2002/82* (2013.01); *C01P 2002/88* (2013.01); *C01P 2004/03* (2013.01); *C01P 2004/04* (2013.01); *C01P 2004/20* (2013.01); *C07J 9/005* (2013.01); *C07J 31/006* (2013.01); *C07J 41/0061* (2013.01); *C07J 41/0088* (2013.01); *C07J 41/0094* (2013.01)

(56) References Cited

U.S. PATENT DOCUMENTS

| | | | | |
|---|---|---|---|---|
| 2013/0281335 | A1* | 10/2013 | Altavilla ................ | B82Y 30/00 508/367 |
| 2015/0329459 | A1* | 11/2015 | Blair ........................ | B01J 27/24 518/728 |

OTHER PUBLICATIONS

Chen et al. (Nanoscale, 2013, 5, 498-502) (Year: 2013).*
Da Young Hwang, et al; "Formation of hexagonal boron nitride nanoscrolls induced by inclusion and exclusion of self-assembling molecules in solution process", Nanoscale; vol. 6, pp. 5686-5690; First published online Apr. 7, 2014.
Da Young Hwang, et al: "Inclusion and exclusion of self-assembled molecules inside graphene scrolls and control of their inner-tube diameter", RSC Adv. vol. 4; pp. 35943-35949; First published online Jul. 2, 2014.
Weilang Liang, et al; "Self-Assembly of J-Aggregate Nanotubes and Their Applications for Sensing Dopamine", Langmuir, 2014, 30(3), pp. 805-811; Publication Date (Web): Jan. 7, 2014.
Tiva Sharifi, et al; "Formation of nitrogen-doped graphene nanoscrolls by adsorption of magnetic $\gamma$-$Fe_2O_3$ nanoparticles", Nature Communications, Aug. 14, 2013; vol. 4,2319, pp. 1-9.
Jian Zheng, et al; "Production of High-Quality Carbon Nanoscrolls with Microwave Spark Assistance in Liquid Nitrogen", Advanced Materials; vol. 23, Issue 21. pp. 2460-2463; First published Apr. 8, 2011.
Weiwei Zhou, et al; "Fabrication of $Co_3O_4$-Reduced Graphene Oxide Scrolls for High-Performance Supercapacitor Electrodes", Phys. Chem, Chem. Phys. vol. 13, Issue 32, pp. 14462-14465; First published online Jul. 7, 2011.
Weiwei Zhou, et al; Supporting Information for "Fabrication of $Co_3O_4$-reduced graphene oxide scrolls for High-Performance Supercapacitor Electrodes", Phys. Chem. Chem. Phys. vol. 13, Issue 32, 11 pages; First published online Jul. 7, 2011.
Shuze Zhu, et al; Hydrogenation enabled scrolling of graphene, Journal of Physics D: Applied Physics; 46; No. 7; Published Jan. 23, 2013; pp. 1-8.
International Search Report dated May 29, 2015; PCT/KR2015/001976.
Weilang Liang et al; "Self-Assembly of J-Aggregate Nanotubes and Their Applications for Sensing Dopamine", Langmuir; vol. 30, pp. 805-811; Published Jan. 7, 2014.

* cited by examiner

[FIG. 1]
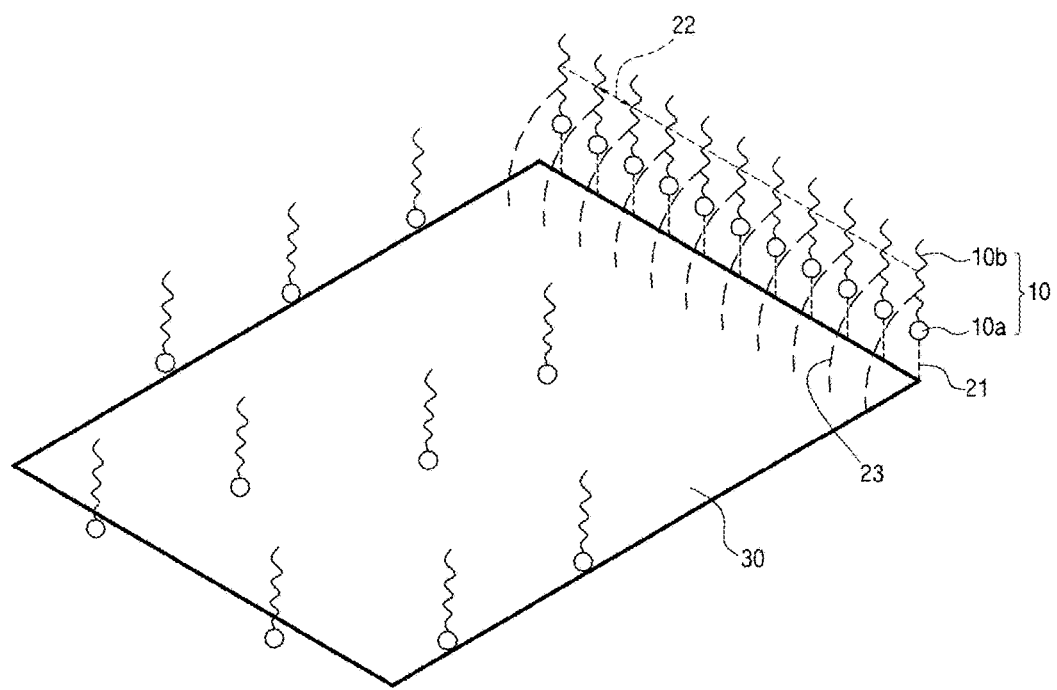
[FIG. 2]
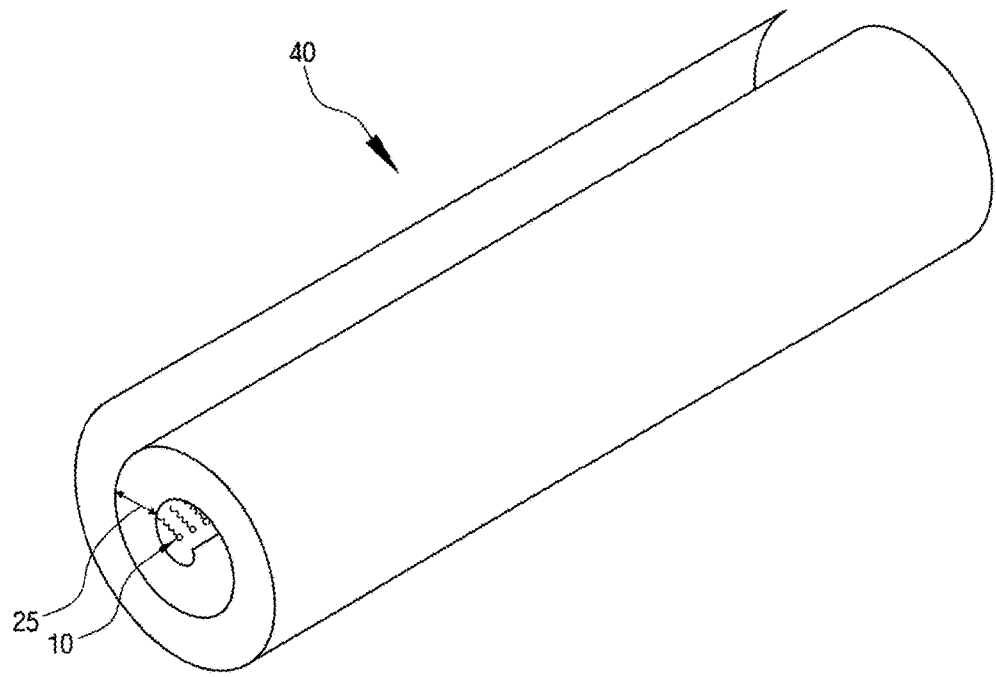

[FIG. 3]
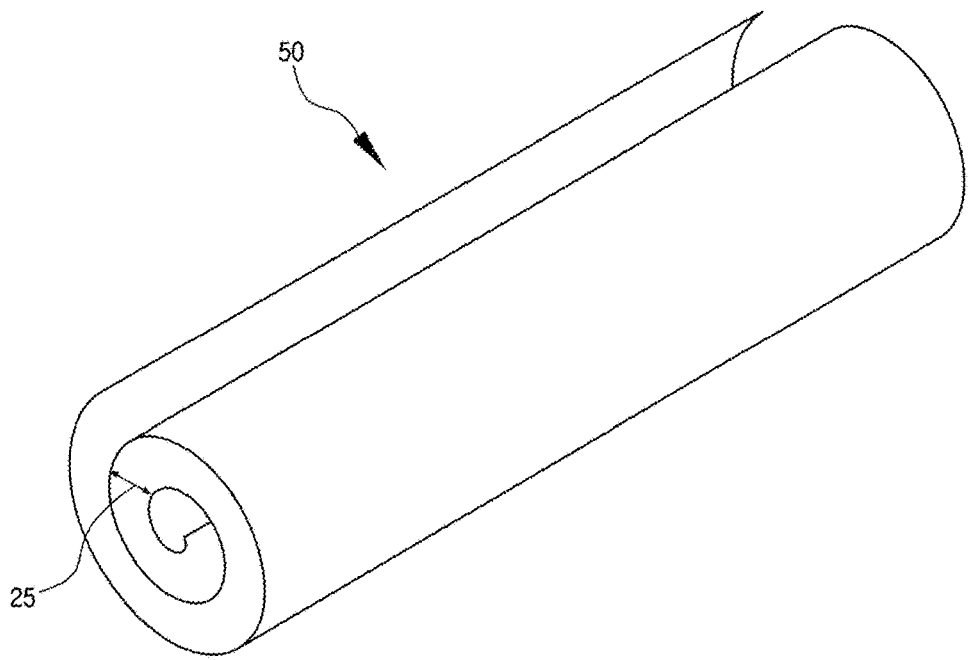
[FIG. 4]
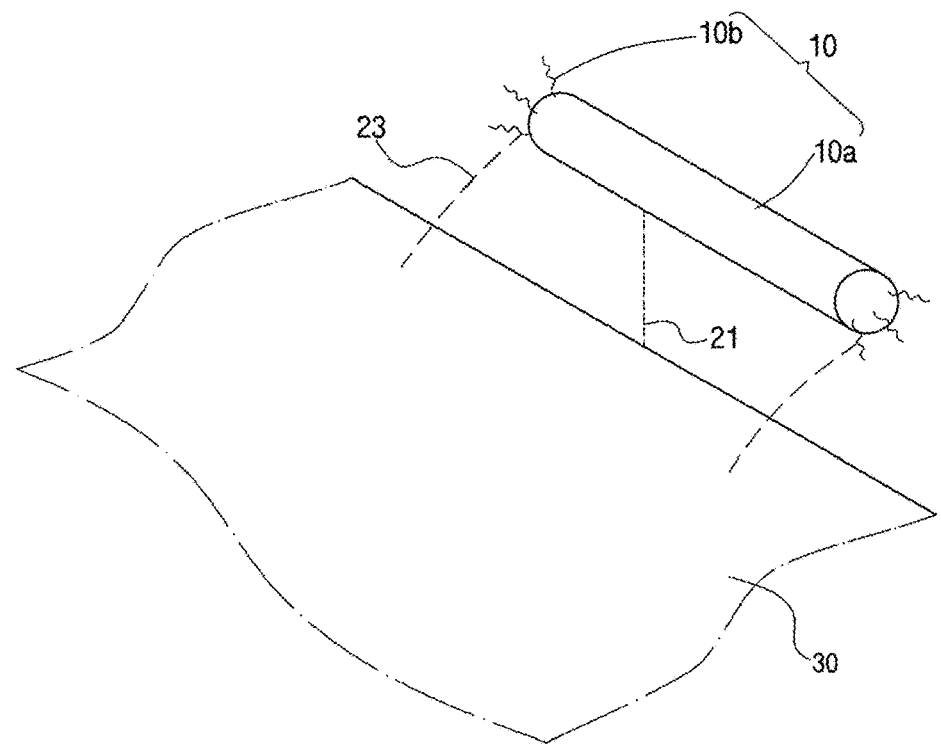

[FIG. 5]
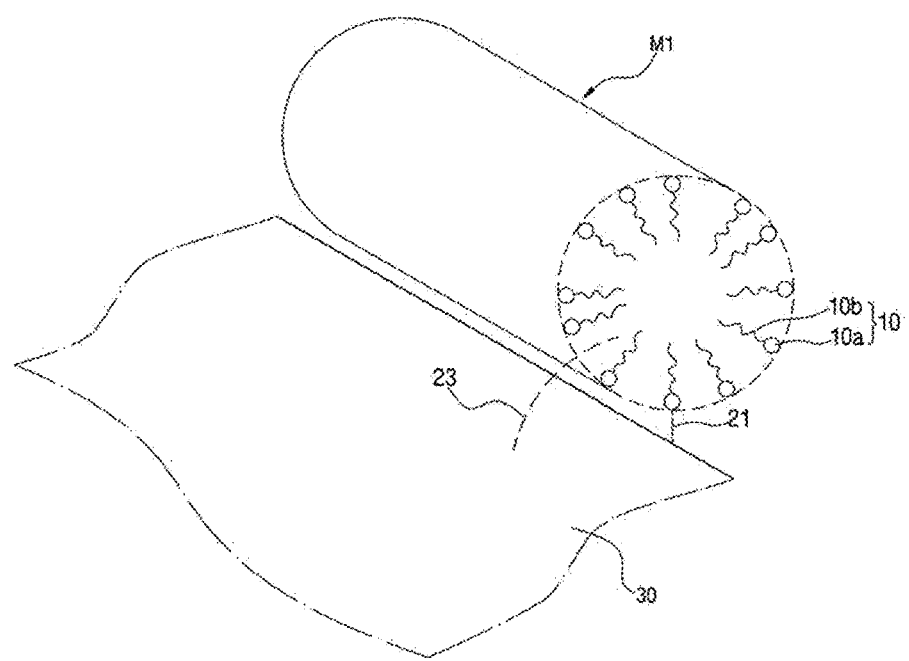
[FIG. 6]
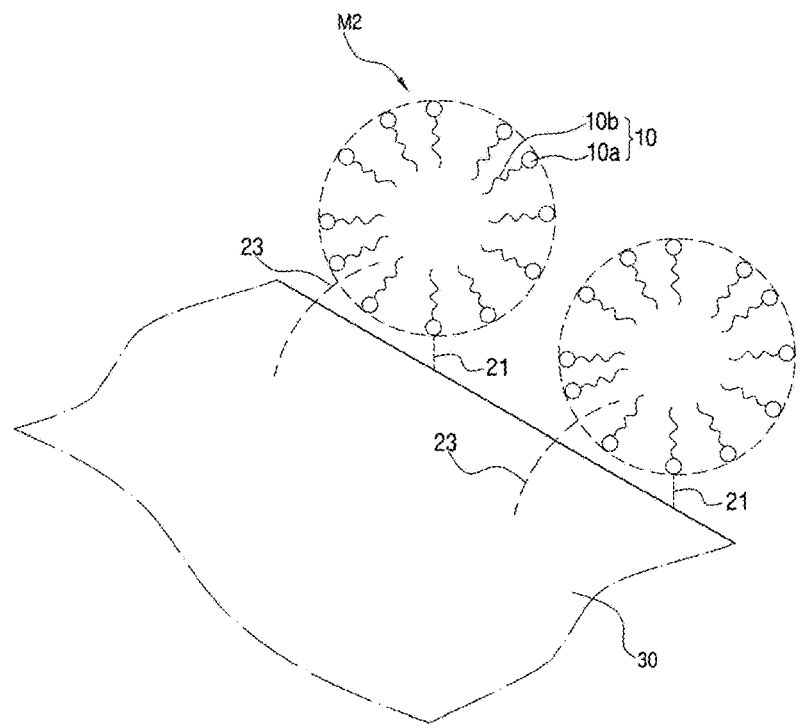

[FIG. 7]
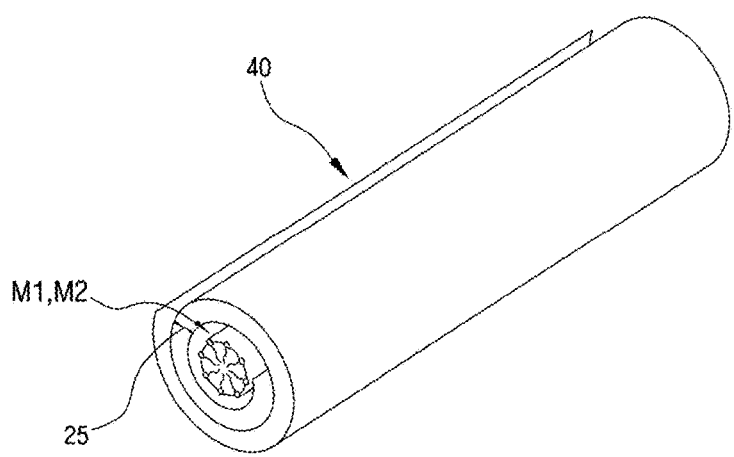
[FIG. 8]
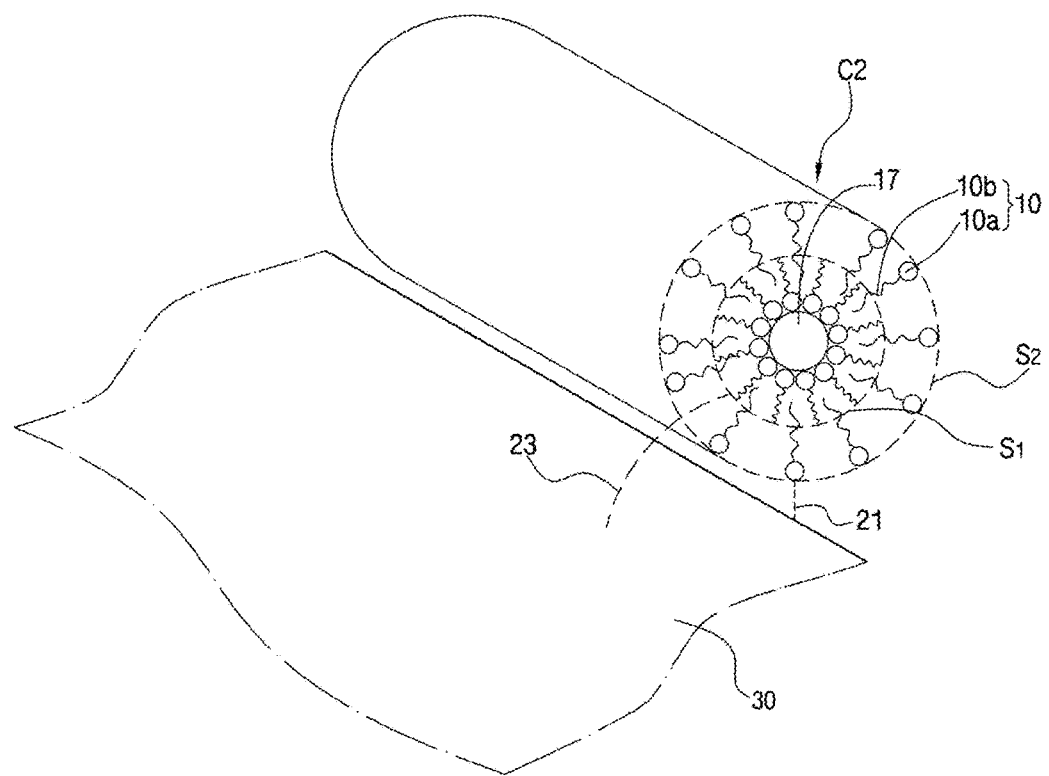

[FIG. 9]
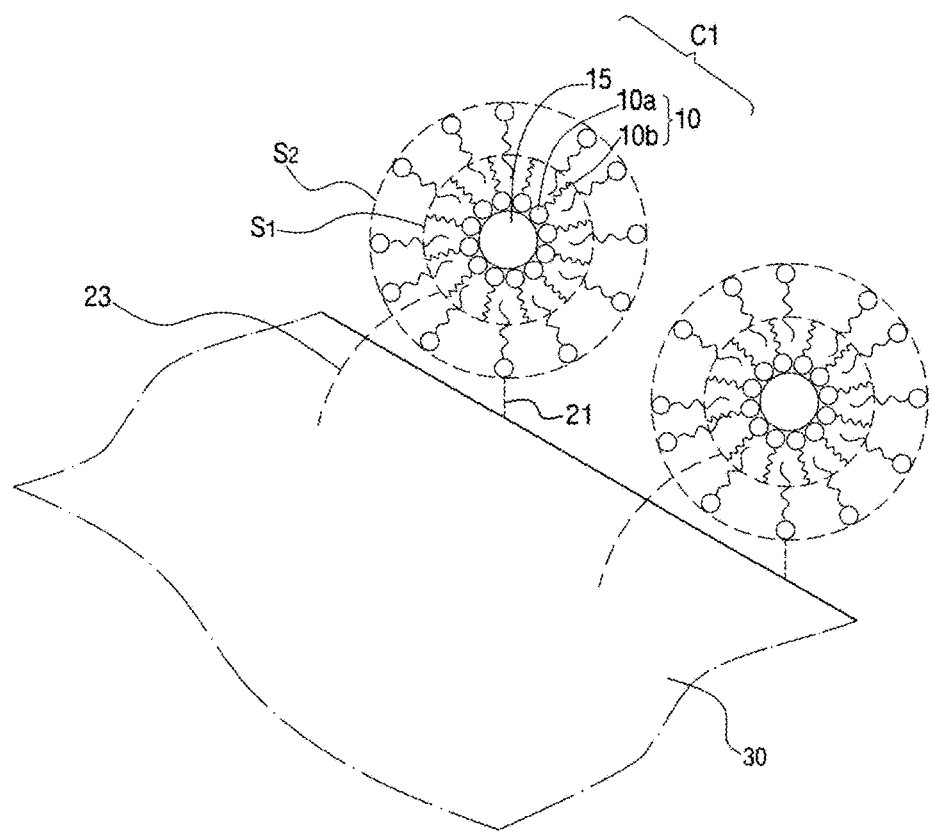
[FIG. 10]
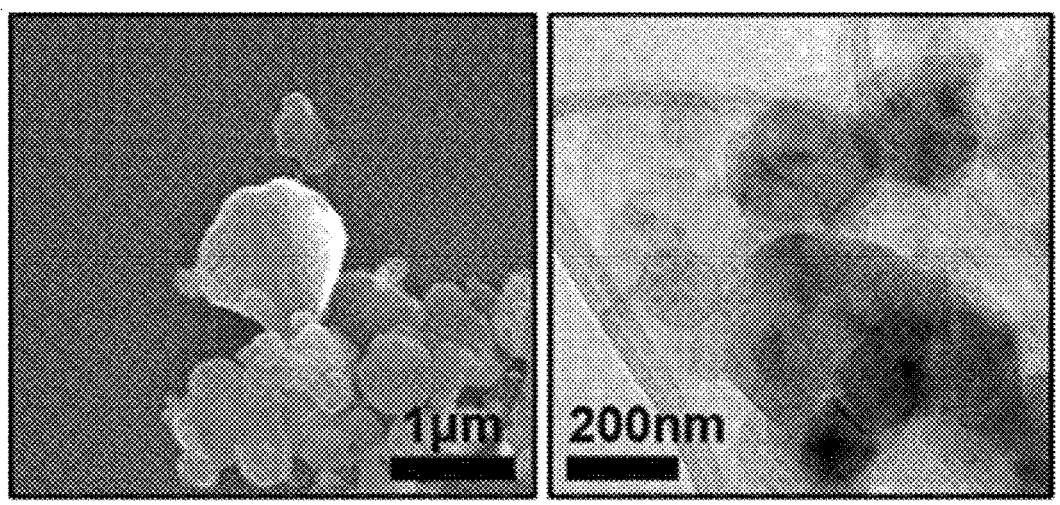

[FIG. 11]
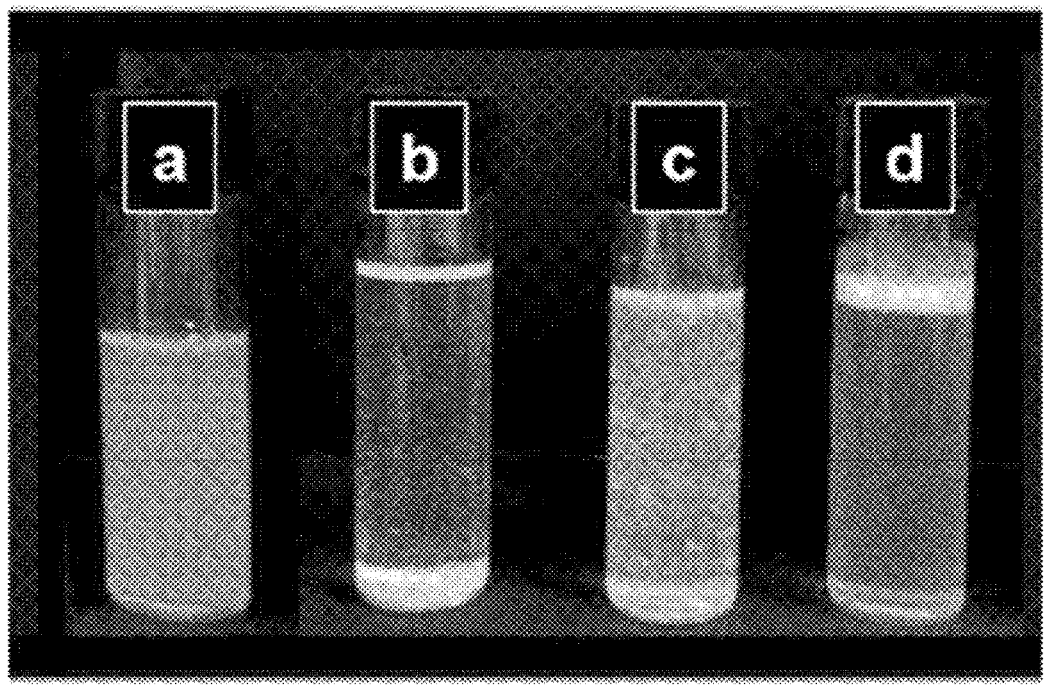
[FIG. 12]
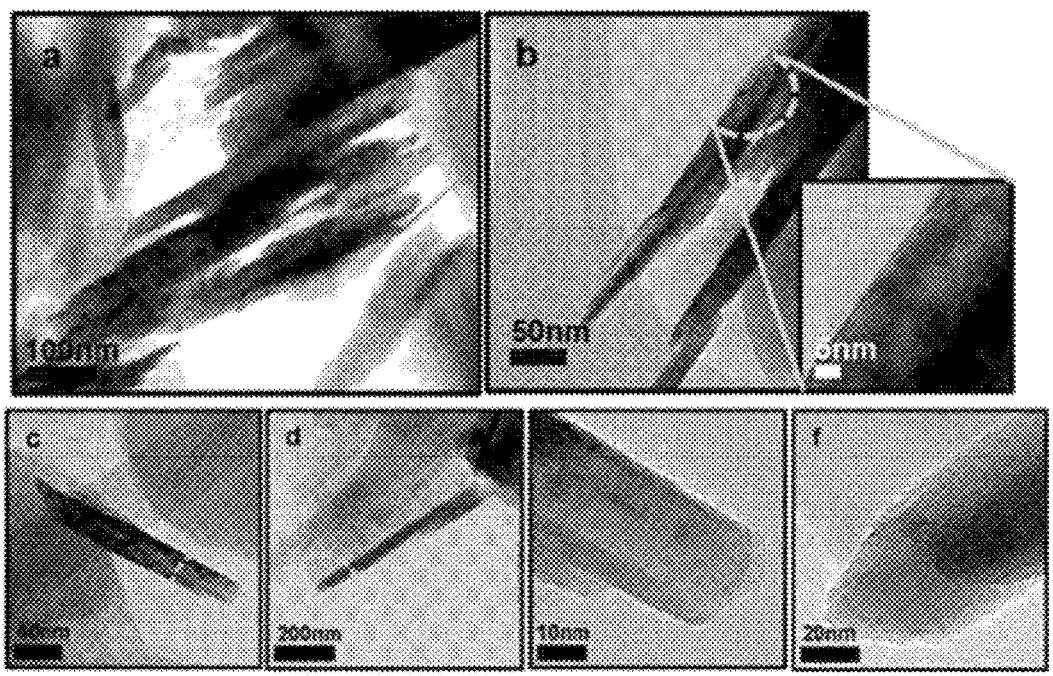

[FIG. 13]
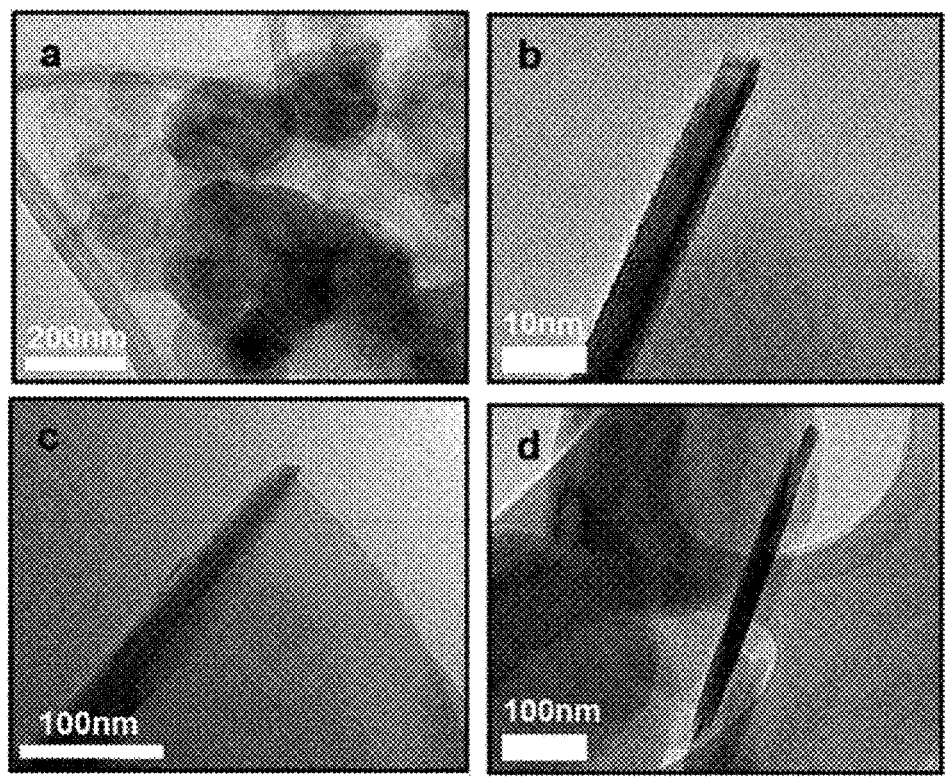
[FIG. 14]
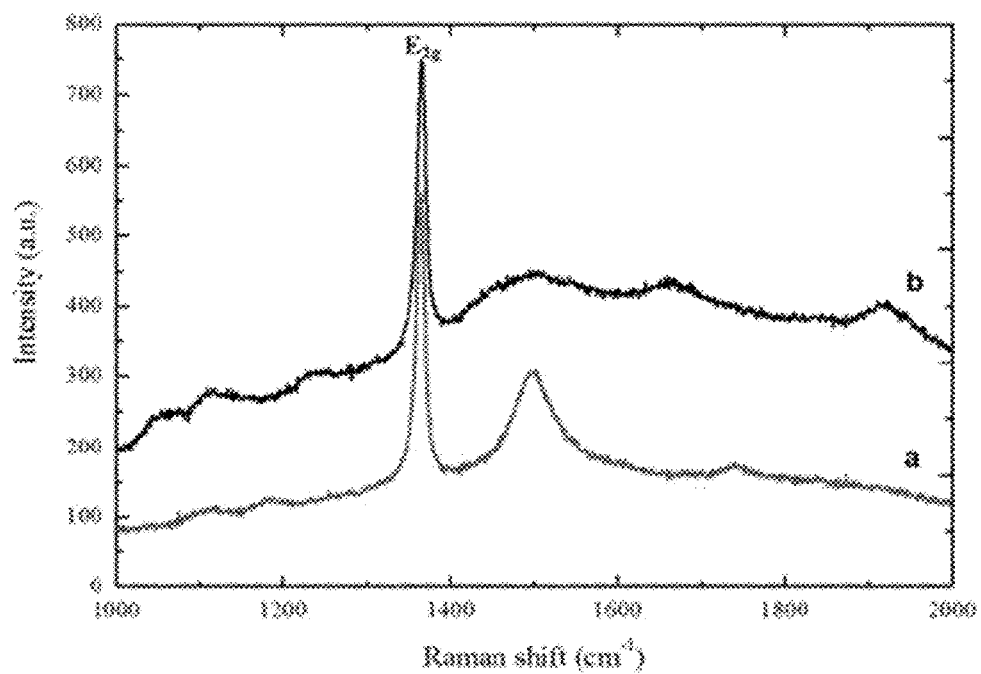

[FIG. 15]
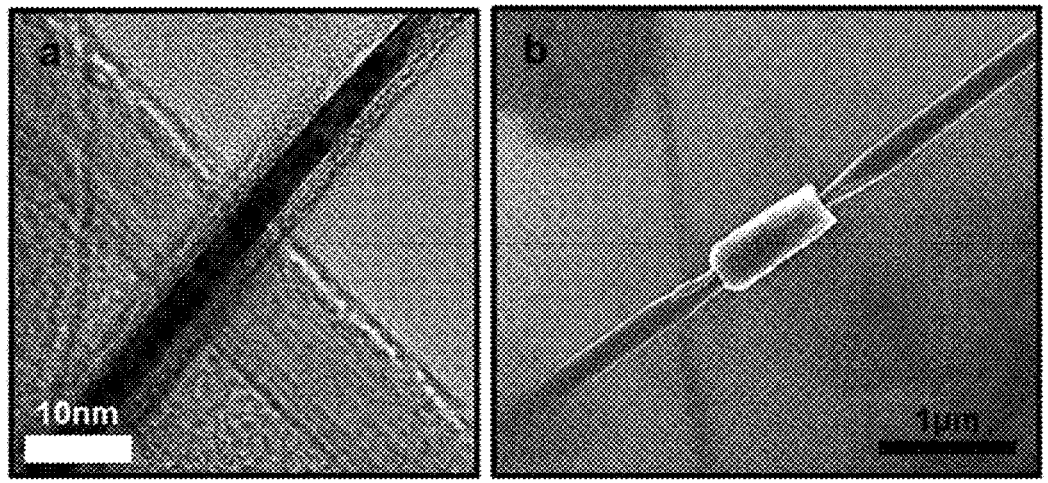
[FIG. 16]
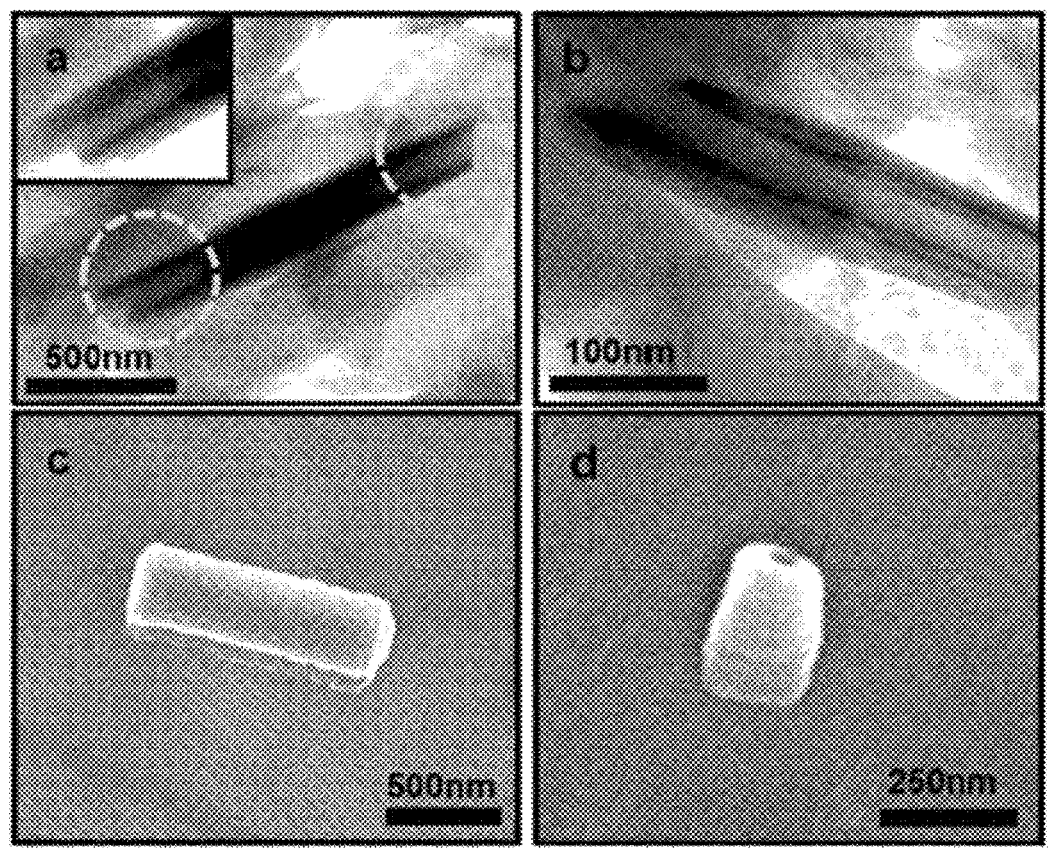

[FIG. 17]
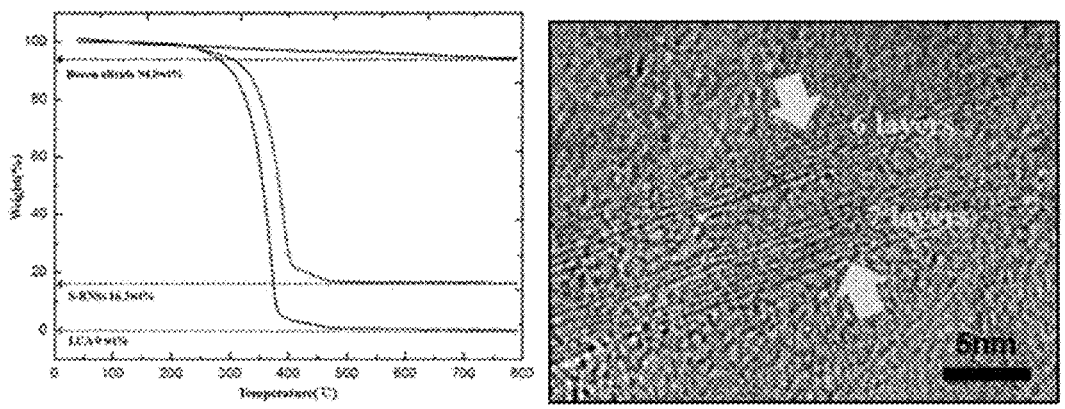
[FIG. 18]
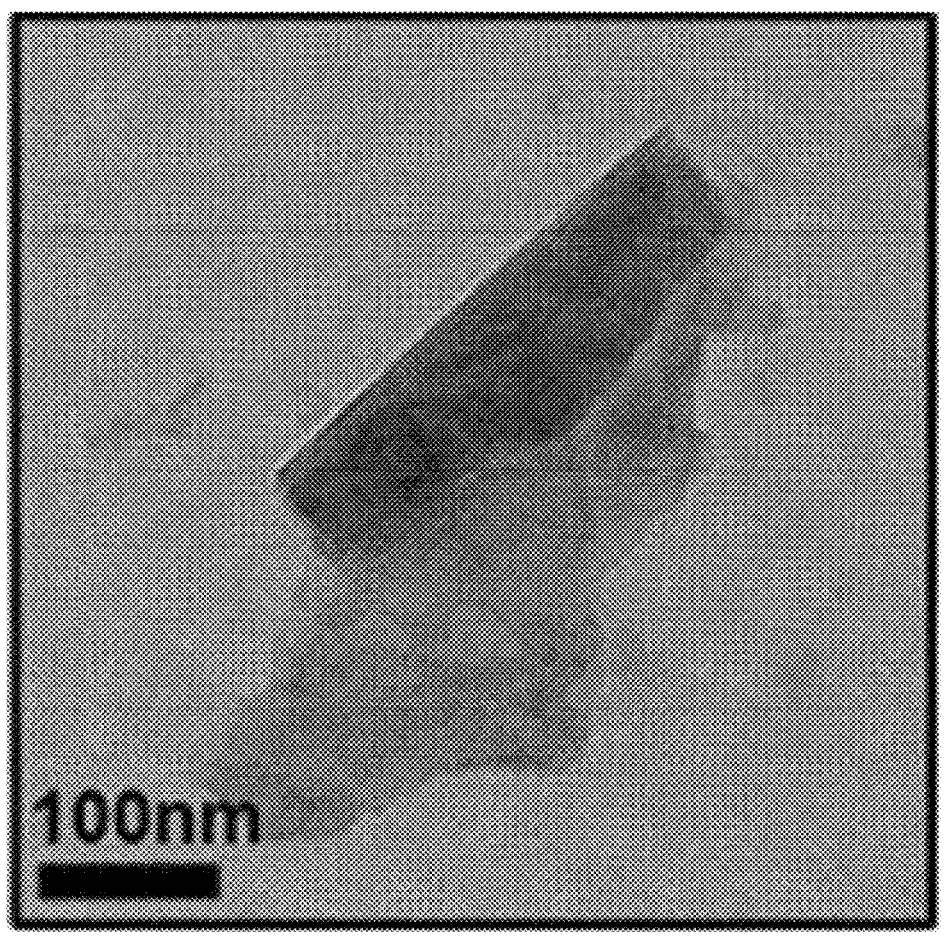

[FIG. 19]
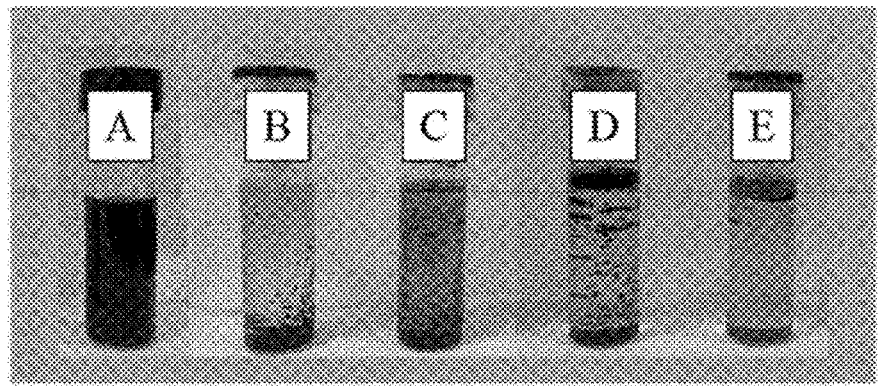
[FIG. 20]
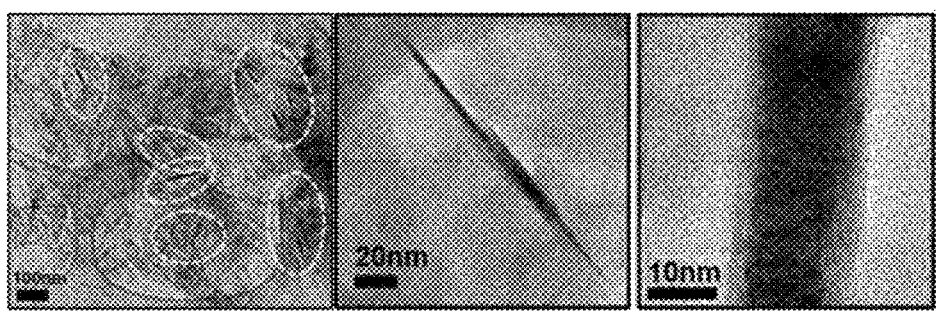
[FIG. 21]
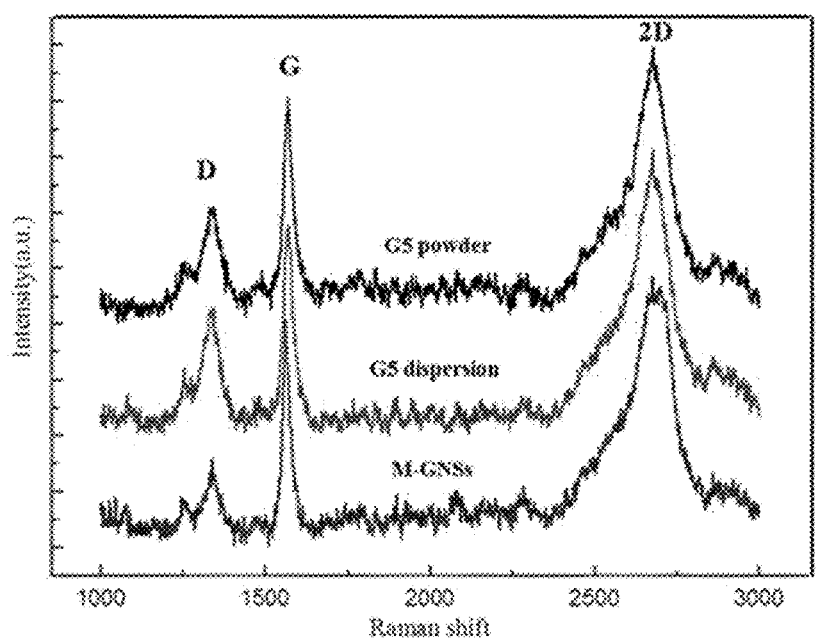

【FIG. 22】
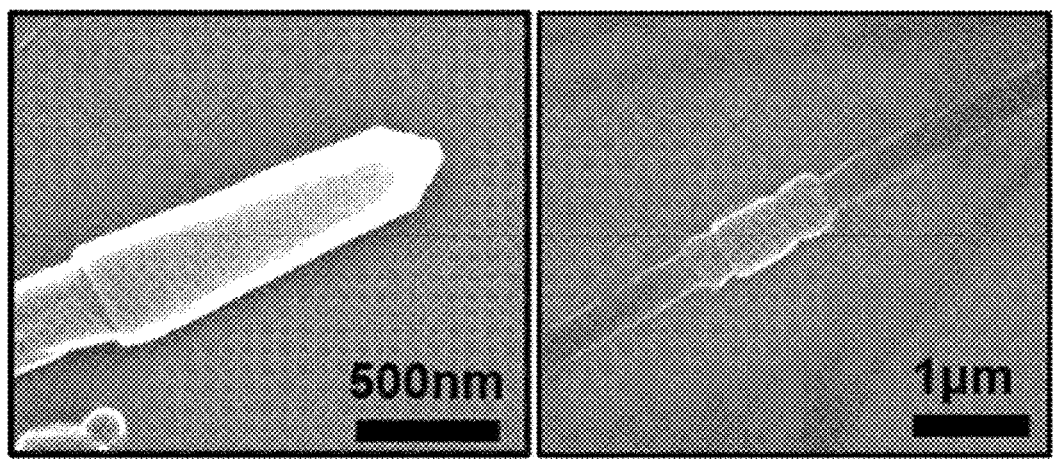
【FIG. 23】
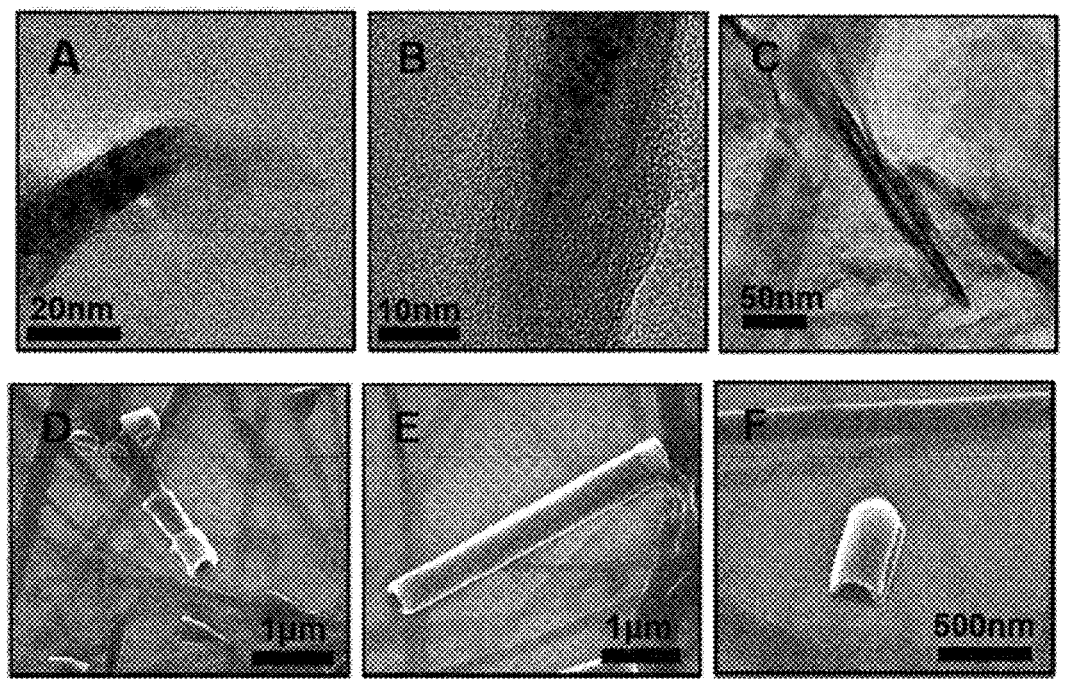

【FIG. 24】
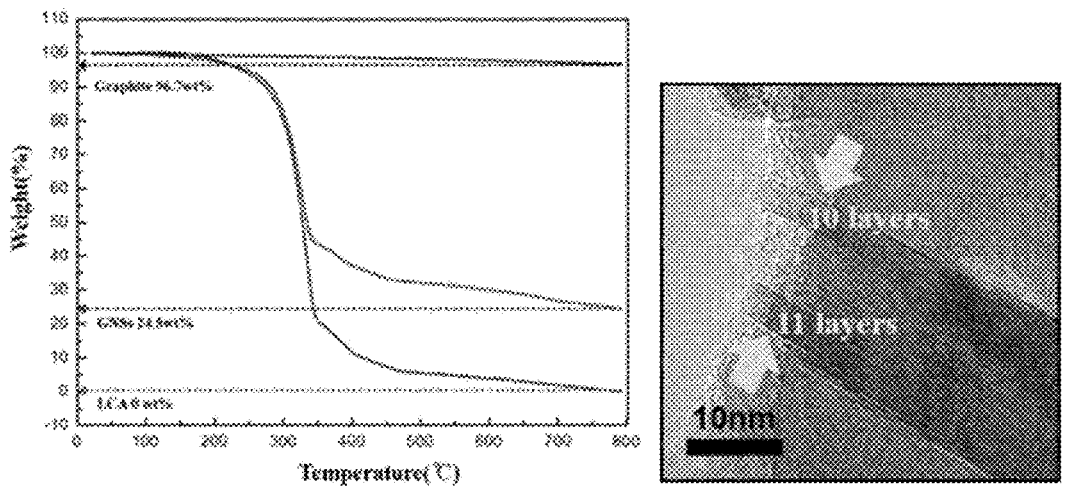
【FIG. 25】
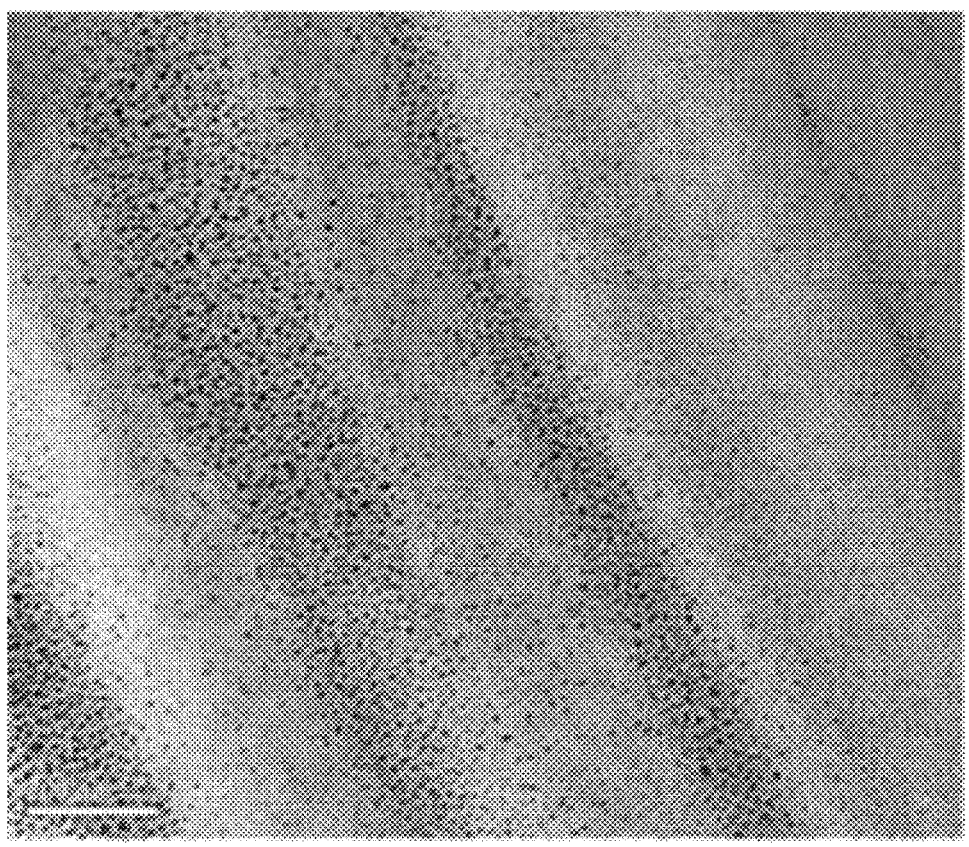

SCROLL COMPOSITE HAVING AMPHIPHILIC SUBSTANCE INSIDE AND METHOD FOR PREPARATION OF THE SAME

TECHNICAL FIELD

The present invention relates to a one-dimensional material, and more particularly, to a scroll.

BACKGROUND ART

Two-dimensional materials such as graphene have different thermal, mechanical and electrical characteristics from three-dimensional bulk materials. Specifically, the two-dimensional materials are known to have excellent mechanical strength, intensity and flexibility, and also have excellent electrical and thermal conductivities. Due to the excellent characteristics of such a two-dimensional material, the two-dimensional material is widely applied to an energy storage device, an energy conversion device, a sensor, a catalyst, and a bio micro electro mechanical system (bio MEMS).

Meanwhile, since a carbon nanotube, which is a one-dimensional material corresponding to an allotrope of graphene, has excellent thermal, mechanical and electrical characteristics, it is also applied in various fields like the two-dimensional material.

Research on the preparation of a composite structure including desired various materials inside the nanotube is progressing. A carbon nanotube composite material has been made by adding a desired material such as fullerene (Brian W. Smith, Marc Monthioux, David E. Luzzi, Encapsulated C60 in carbon nanotubes, Nature, VOL 396, 26 Nov. 1998), an organic material (TAISHI TAKENOBU et al., Stable and controlled amphiphilic doping by encapsulation of organic molecules inside carbon nanotubes, Nature Materials, VOL 2, OCTOBER, 2003), a metal (Jean-Philippe et al., Selective Deposition of Metal Nanoparticles Inside or Outside Multiwalled Carbon Nanotubes, ACSNano, VOL. 3, NO. 8, 2081-2089, 2009) into a carbon nanotube. However, it was not easy to prepare the nanotube with open ends, and to remove a desired material after addition thereof.

DISCLOSURE

Technical Problem

Therefore, an object to be solved by the present invention is to provide a method for forming a one-dimensional scroll by inducing the roll-up of a two-dimensional material, and the one-dimensional scroll formed thereby.

Technical problems of the present invention are not limited to those described above, and other technical problems that have not been described will be fully understood to those of ordinary skill in the art from the descriptions that will be described below.

Technical Solution

One aspect of the present invention provides a scroll composite. The scroll composite includes a two-dimensional material scroll with open ends. An amphiphilic substance is disposed inside the scroll.

The two-dimensional material may be a single substance selected from the group consisting of graphene, graphene oxide, boron nitride, boron carbon nitride (BCN), tungsten oxide ($WO_3$), tungsten sulfide ($WS_2$), molybdenum sulfide ($MoS_2$), molybdenum telluride ($MoTe_2$), and manganese oxide ($MnO_2$), or a composite substance including a stack of two or more thereof.

The amphiphilic substance may be a surfactant, a bile acid, a bile acid salt, a hydrate of a bile acid salt, a bile acid ester, a bile acid derivative, or a bacteriophage.

The amphiphilic substance may be in a self-assembled structure. Hydrophilic portions of the amphiphilic substances may be exposed at the exterior of the self-assembled structure. The self-assembled structure may have a spherical, rod-shaped or fiber-shaped structure.

The self-assembled structure of the amphiphilic substance may include core particles and one or more shells including the amphiphilic substances self-assembled on the core particle. A hydrophilic portion of the amphiphilic substance may be exposed at the exterior of the self-assembled structure of the amphiphilic substance. The core particle may have a spherical or rod-shaped structure. The core particle may be a metal particle, a metal oxide particle, or a bacteriophage.

One aspect of the present invention provides a two-dimensional material scroll. The two-dimensional material scroll has a structure in which a two-dimensional material is rolled up, and which has van der Waals interactions between adjacent two-dimensional material sheets and has open ends. The two-dimensional material scroll may be a hollow scroll having an empty inside.

One aspect of the present invention provides a method for preparing a two-dimensional material scroll. First, a two-dimensional material is provided. The two-dimensional material is scrolled by providing an amphiphilic substance having a hydrophilic portion and a hydrophobic portion on the two-dimensional material. As a result, the amphiphilic substance is disposed inside the scrolled structure, thereby forming a scroll composite.

The two-dimensional material may be dispersed in a solvent, thereby providing a two-dimensional material dispersion. The providing of the amphiphilic substance may be mixing an amphiphilic substance solution prepared by dissolving the amphiphilic substance in a solvent with the two-dimensional material dispersion. The amphiphilic substance solution may be heated before being mixed with the two-dimensional material dispersion. In addition, the heated amphiphilic substance solution may be cooled before being mixed with the two-dimensional material dispersion.

The amphiphilic substance solution may include core particles.

At least a part of the amphiphilic substance may be removed by solvent treatment and/or thermal treatment on the scroll composite, thereby forming a hollow scroll. The solvent may be one which dissolves the amphiphilic substance. The thermal treatment may be performed at 200 to 800° C.

Advantageous Effects

As described above, according to the present invention, a one-dimensional scroll may be easily formed by inducing the roll-up of a two-dimensional material using an amphiphilic substance. Also, the one-dimensional scroll may be provided.

DESCRIPTION OF DRAWINGS

FIGS. 1 to 3 are the schematic diagrams sequentially illustrating a method for preparing a scroll according to an exemplary embodiment of the present invention.

FIG. 4 is the schematic diagram illustrating a method for preparing a scroll according to another exemplary embodiment of the present invention.

FIGS. 5, 6 and 7 are the schematic diagrams illustrating a method for preparing a scroll according to still another exemplary embodiment of the present invention.

FIGS. 8 and 9 are the schematic diagrams illustrating a method for preparing a scroll according to yet another exemplary embodiment of the present invention.

FIG. 10 shows the scanning electron microscope (SEM) image (a) and transmission electron microscope (TEM) image (b) of a boron nitride dispersion obtained during the process of Preparation Example 18.

FIG. 11 shows the image (a) of the boron nitride dispersion obtained during the process of Preparation Example 18, and the image (c) of a mixed solution of the dispersion and a solution of a bile acid derivative of Formula 4.

FIG. 12 shows the TEM image (a) and high resolution (HR)-TEM images (b, c, d, e, f) of boron nitride scroll composite materials obtained in Preparation Example 18.

FIG. 13 shows the TEM image (a) of the boron nitride dispersion and the TEM images (b, c and d) of boron nitride scroll composite materials, obtained during the process of Preparation Example 18.

FIG. 14 shows the Raman graph of exfoliated h-BN (a) obtained during the process of Preparation Example 18 and a BN scroll composite material (b) obtained in Preparation Example 18.

FIG. 15 shows the HR-TEM images of a BN scroll composite material (a) obtained in Preparation Example 18 and a BN scroll composite material (b) obtained in Preparation Example 19.

FIG. 16 shows the SEM images (a, b) and TEM images (c, d) of BN scrolls obtained according to Preparation Examples 79 and 80.

FIG. 17 shows the TGA graph (a) and TEM image (b) of boron nitride, the bile acid derivative of Formula 4, and the BN scroll composite obtained according to Preparation Example 18, obtained by thermal treatment in a nitrogen atmosphere.

FIG. 18 shows the SEM image of a graphene dispersion obtained during the process of Preparation Example 1.

FIG. 19 shows the image (A) of the graphene dispersion obtained during the process of Preparation Example 1, and the image (D) of a mixed solution of the dispersion and the bile acid derivative of Formula 4.

FIG. 20 shows the HR-TEM images of graphene scroll composite materials obtained in Preparation Example 1.

FIG. 21 shows the Raman graph of an exfoliated graphene (G5 dispersion) obtained during the process of Preparation Example 2, graphene powder and a graphene scroll composite material (M-GNSs) obtained in Preparation Example 2.

FIG. 22 shows the SEM images of graphene scroll composite materials obtained during the process of Preparation Example 2.

FIG. 23 shows the HR-TEM images (A, B, C) of a graphene scroll obtained according to Preparation Example 74, and the SEM images (D, E, F) of a graphene scroll obtained according to Preparation Example 75.

FIG. 24 shows the TGA graph (a) and TEM image (b) of graphite, the bile acid derivative of Formula 4, and the graphene scroll composite obtained according to Preparation Example 1, obtained by thermal treatment in a nitrogen atmosphere.

FIG. 25 is the SEM image of an amphiphilic substance solution obtained during the process of Preparation Example 17.

MODES OF THE INVENTION

Hereinafter, to more fully explain the present invention, exemplary embodiments according to the present invention will be described in further detail with reference to the accompanying drawings. However, the present invention may be embodied in different forms and should not be understood as being limited to the examples, which will not be described herein.

FIGS. 1 to 3 are the schematic diagrams sequentially illustrating a method for preparing a scroll according to an exemplary embodiment of the present invention.

Referring to FIG. 1, a two-dimensional material 30 is provided. The two-dimensional material 30 refers to a very thin material having a nanometer-scale thickness, for example, a material having 1 to 10 atomic layers, for example 1 to 5 atomic layers, and for further example 1 to 2 atomic layers. Each atomic layer may have a crystal structure, for example, a hexagonal honeycomb shape.

The two-dimensional material 30 may be a composite material including a single substance selected from the group consisting of graphene, graphene oxide, boron nitride, boron carbon nitride (BCN), tungsten oxide ($WO_3$), tungsten sulfide ($WS_2$), molybdenum sulfide ($MoS_2$), molybdenum telluride ($MoTe_2$), and manganese oxide ($MnO_2$), or a composite material including a stack of two or more thereof. The composite material may be one in which boron nitride, boron carbon nitride or molybdenum sulfide is stacked on graphene, or one in which molybdenum sulfide is stacked on boron nitride.

Edges of such a two-dimensional material 30 have lower stability due to higher surface energy than an in-plane region, and thus enables easy oxidation.

The two-dimensional material 30 may be dispersed in a solvent, thereby preparing a two-dimensional material dispersion. Specifically, the two-dimensional material dispersion may be obtained by dispersing two-dimensional material powder in a solvent by mechanical stirring or sonication, and then performing centrifugation. The solvent may be one selected from the group consisting of water, methanol, ethanol, isopropyl alcohol, toluene, benzene, hexane, heptane, m-cresol, ethyl acetate, carbon disulfide, dimethylsulfoxide, dichloromethane, dichlorobenzene, chloroform, carbon tetrachloride, acetone, tetrahydrofuran, dimethylacetamide, N-methylpyrrolidone, and acetic acid, or a combination of two or more thereof. The solvent may be suitably selected depending on the two-dimensional material to easily disperse the two-dimensional material.

An amphiphilic substance 10 may be provided on the two-dimensional material 30. Specifically, the amphiphilic substance 10 may be added into the solvent in which the two-dimensional material 30 is dispersed, or an amphiphilic substance solution prepared by dissolving the amphiphilic substance 10 in a solvent may be mixed with the two-dimensional material dispersion. In addition, the amphiphilic substance solution may be heated before being mixed with the two-dimensional material dispersion. In this case, the amphiphilic substance solution may be cooled while being mixed with the two-dimensional material dispersion at room temperature, and thus the amphiphilic substance 10 may be easily self-assembled at an edge of the two-dimensional material 30.

In the amphiphilic substance solution, the amphiphilic substance may be contained, for example, at a concentration of 0.001 g/mL to 1 g/mL, but the present invention is not limited thereto. However, according to the concentration of the amphiphilic substance, an amount of scroll composites 40 (FIG. 2), which will be described below, may be adjusted, the composites being generated after the two-dimensional material dispersion is mixed with the amphiphilic substance solution.

The solvent used in the amphiphilic substance solution may be one selected from the group consisting of water, methanol, ethanol, isopropyl alcohol, toluene, benzene, hexane, heptane, m-cresol, ethyl acetate, carbon disulfide, dimethylsulfoxide, dichloromethane, dichlorobenzene, chloroform, carbon tetrachloride, acetone, tetrahydrofuran, dimethylacetamide, N-methylpyrrolidone, dimethylformamide and acetic acid, or a combination of two or more thereof, and may be the same as or different from that used for the two-dimensional material dispersion.

The amphiphilic substance 10 may be a substance having both of a hydrophilic portion 10a and a hydrophobic portion 10b in one molecule. Specifically, the amphiphilic substance 10 may be an organic material such as a surfactant, a bile acid, a bile acid salt, a hydrate of a bile acid salt, a bile acid ester, a bile acid derivative, or a bacteriophage.

The surfactant may include one or more compounds selected from the group consisting of sodium dodecyl sulfate (SDS), ammonium lauryl sulfate, sodium laureth sulfate, alkyl benzene sulfonate, cetyl trimethylammonium bromide (CTAB), hexadecyl trimethyl ammonium bromide, an alkyltrimethylammonium salt, cetylpyridinium chloride (CPCl), polyethoxylated tallow amine (POEA), benzalkonium chloride (BAC), benzethonium chloride (BZT), dodecyl betaine, dodecyl dimethylamine oxide, cocamidopropyl betaine, alkyl poly(ethylene oxide), a poloxamer, a poloxamine, alkyl polyglucoside, cetyl alcohol, sodium deoxycholate, cocamide MEA, cocamide DEA, sorbitan ester, polyoxyethylene sorbitan fatty acid ester, sucrose fatty acid ester, polyethyelene glycol hydroxystearate, polyoxyethylene glycolated natural or hydrogenated castor oil, a polyoxyethylene-polyoxypropylene copolymer, a synthetic vitamin E derivative, polyoxyethylene alkyl ester, fatty acid microgol glyceride, polyglyceryl fatty acid ester, and a silicone-based surfactant. The one or more compounds may include one or more types of compounds, or the same type of two or more compounds.

The bile acid may be, for example, represented by Formula 1 below.

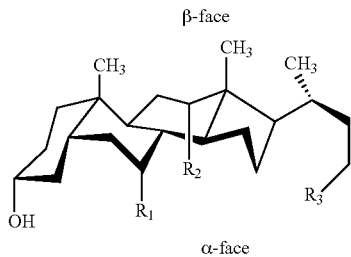

[Formula 1]

In Formula 1, $R_1$ and $R_2$ may each be independently —H or —OH, $R_3$ may be —(CONH—(CH$_2$)$_{n1}$)$_{n2}$—Y$_1$, n1 may be 1 or 2, n2 may be 1 or 0, and $Y_1$ may be —COOH or —SO$_3$H. In one example, $R_1$, $R_2$, and $R_3$ may be the same as described in Table 1.

TABLE 1

| $R_1$ | $R_2$ | $R_3$ | Bile acid |
|---|---|---|---|
| —OH | —OH | —COOH | Cholic Acid |
| —OH | —H | —COOH | Chenodeoxycholic Acid |
| —H | —OH | —COOH | Deoxycholic Acid |
| —H | —H | —COOH | Lithocholic Acid |
| —OH | —OH | —CONH—CH$_2$—COOH | Glycocholic Acid |
| —OH | —OH | —CONH—(CH$_2$)$_2$—SO$_3$H | Taurocholic Acid |
| —OH | —H | —CONH—CH$_2$—COOH | Glycochenodeoxycholic Acid |
| —OH | —H | —CONH—(CH$_2$)$_2$—SO$_3$H | Taurochenodeoxycholic Acid |
| —H | —OH | —CONH—CH$_2$—COOH | Glycodeoxycholic Acid |
| —H | —OH | —CONH—(CH$_2$)$_2$—SO$_3$H | Taurodeoxycholic Acid |
| —H | —H | —CONH—CH$_2$—COOH | Glycolithocholic Acid |
| —H | —H | —CONH—(CH$_2$)$_2$—SO$_3$H | Taurolithocholic Acid |

Another example of the bile acid may be dehydrocholic acid, hyodeoxycholic acid, or ursodeoxycholic acid.

The bile acid salt may be a metal salt of the bile acid, and specifically, a bile acid sodium salt. In one example, the bile acid salt may be sodium glycochenodeoxycholate, sodium taurochenodeoxycholate, sodium taurocholate, sodium dehydrocholate, or sodium deoxycholate.

Also, the hydrate of a bile acid salt may be a hydrate of the bile acid metal salt, and specifically, a hydrate of the bile acid sodium salt. In one example, a hydrate of a bile acid salt may be sodium taurocholate hydrate or sodium cholate hydrate.

The bile acid ester may be hyodeoxycholic acid methyl ester.

The bile acid derivative may be represented by Formula 2 below.

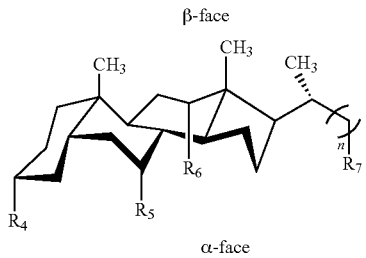

[Formula 2]

In Formula 2, n is 0, 1 or 2, and $R_4$ to $R_7$ are each independently a group represented by Formula 3.

$-(B_1)_m-(L_1)_n-G_1$ [Formula 3]

In Formula 3, $B_1$ is one group selected from the group consisting of

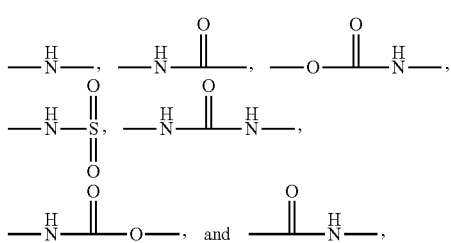

$L_1$ is a linker of —W$_1$—, -Q$_1$-, -Q$_2$-W$_2$—, —W$_3$-Q$_3$-W$_4$—, or —W$_5$-Q$_4$-W$_6$-Q$_5$-Q$_6$-, W$_1$, W$_2$, W$_3$, W$_4$, W$_5$, and W$_6$ are each independently

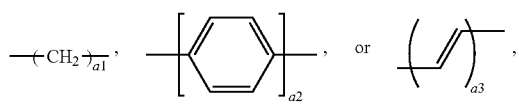

$a_1$ to $a_3$ are each an integer of 1 to 4, $Q_1$, $Q_2$, $Q_3$, $Q_4$, $Q_5$, and $Q_6$ are each independently

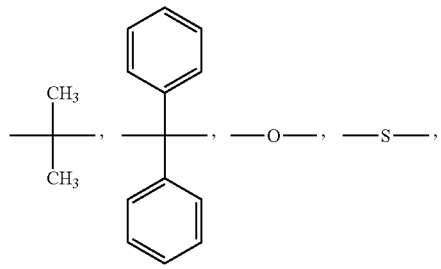

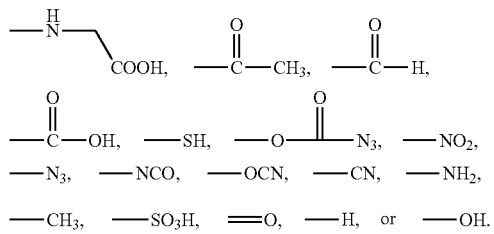

and $G_1$ is a group represented by

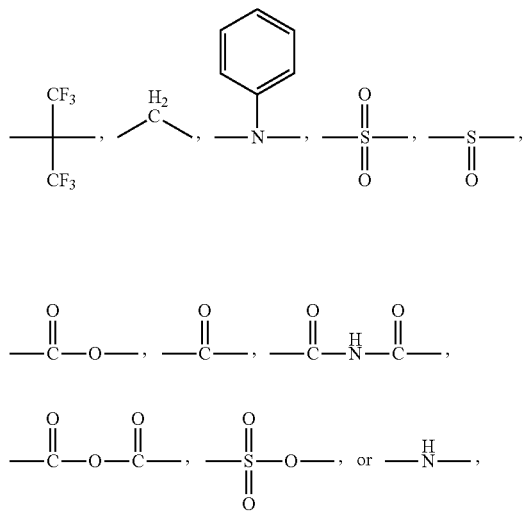

In addition, m is 0 or 1, n is 0 or 1, and when both of m and n are 0, $G_1$ is directly linked without $B_1$ and $L_1$.

In one example, $R_4$, $R_5$, and $R_6$ may each be independently —H, —OH, —$SO_3H$, —$OSO_3H$, or =O, and $R_7$ may be a group represented by Formula 3.

The bile acid derivative may be any one of the bile acid derivatives of Formulas 4 to 20.

[Formula 4]

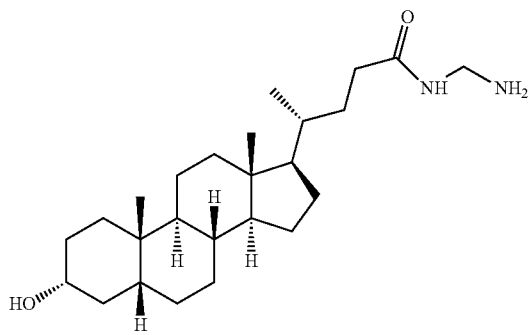

(R)-N-(aminomethyl)-4-((3R,5R,8R,9S,10S,13R,14S,17R)-3-hydroxy-10,13-dimethylhexadecahydro-1H-cyclopenta[a]phenanthren-17-yl)pentanamide

[Formula 5]

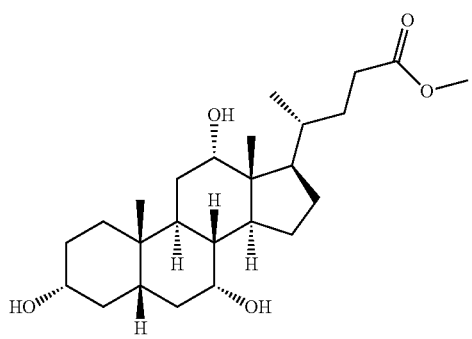

(R)-methyl-4-((3R,5S,7R,8R,9S,10S,12S,13R,14S,17R)-3,7,12-trihydroxy-10,13-dimethylhexadecahydro-1H-cyclopenta[a]phenanthren-17-yl)pentanoate

[Formula 6]

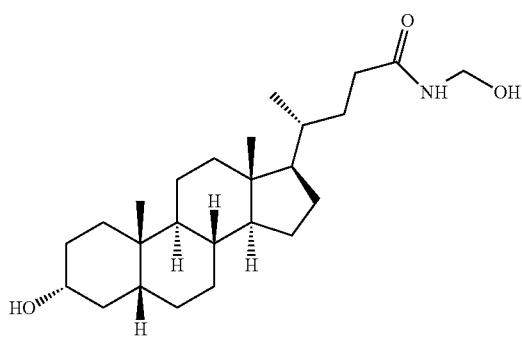

(R)-4-((3R,5R,8R,9S,10S,13R,14S,17R)-3-hydroxy-10,13-dimethylhexadecahydro-1H-cyclopenta[a]phenanthren-17-yl)-N-(hydroxymethyl)pentanamide 5β-cholanie acid-3α,12α-diol 3-acetate methyl ester

[Formula 7]

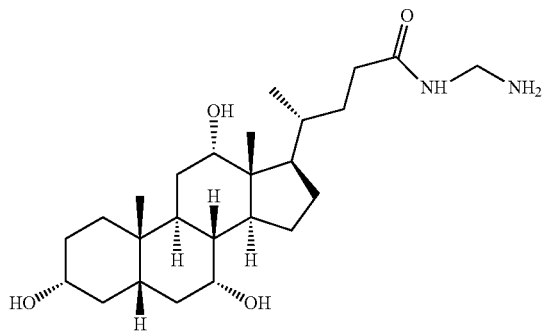

(R)-N-(aminomethyl)-4-((3R,5S,7R,8R,9S,10S,12S,13R,
14S,17R)-3,7,12-trihydroxy-10,13-dimethylhexadeca-
hydro-1H-cyclopenta[a]phenanthren-17-yl)pentanamide

[Formula 10]

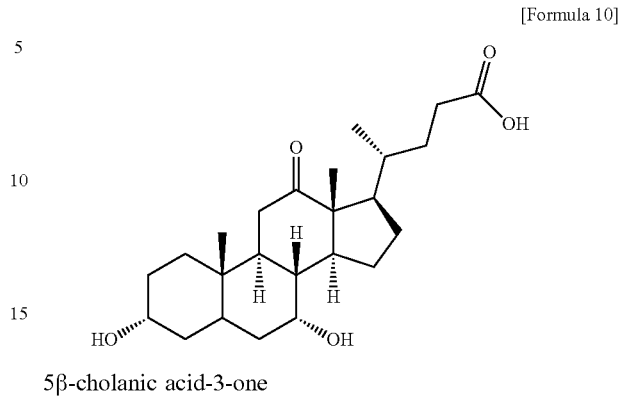

5β-cholanic acid-3-one

[Formula 11]

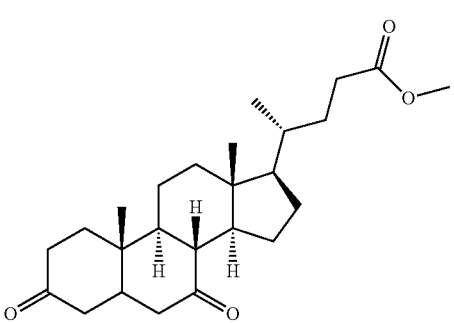

5β-cholanic acid 3,7-dione methyl ester

[Formula 8]

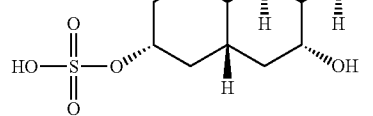

(R)-4-((3R,5R,7R,8R,9S,10S,13R,14S,17R)-7-hydroxy-10,
13-dimethyl-3-(sulfooxy)hexadecahydro-1H-cyclopenta
[a]phenanthren-17-yl)pentanoic acid

[Formula 12]

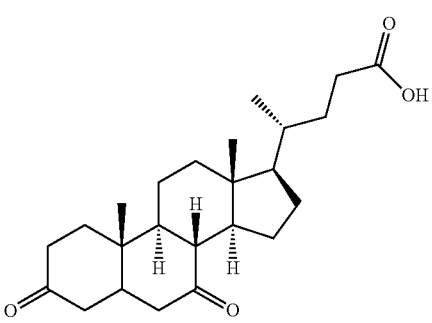

5β-cholanic acid-3,7-dione

[Formula 9]

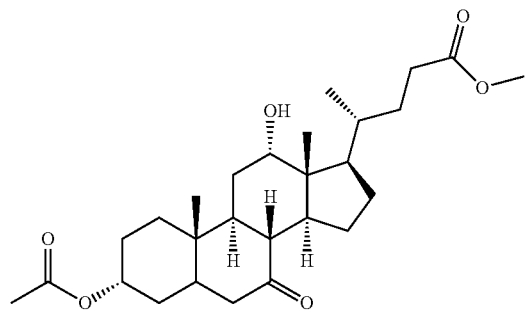

[Formula 13]

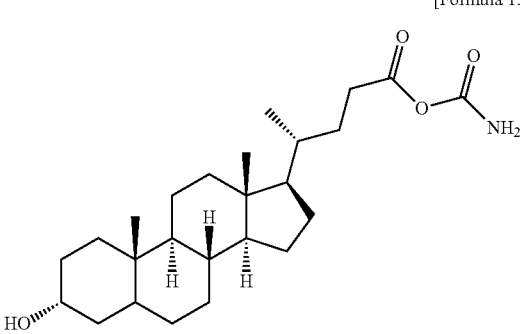

carbamic(4R)-4-((3R,8R,9S,10S,13R,14S,17R)-3-hydroxy-
10,13-dimethylhexadecahydro-1H-cyclopenta[a]phenan-
thren-17-yl)pentanoic anhydride

[Formula 14]

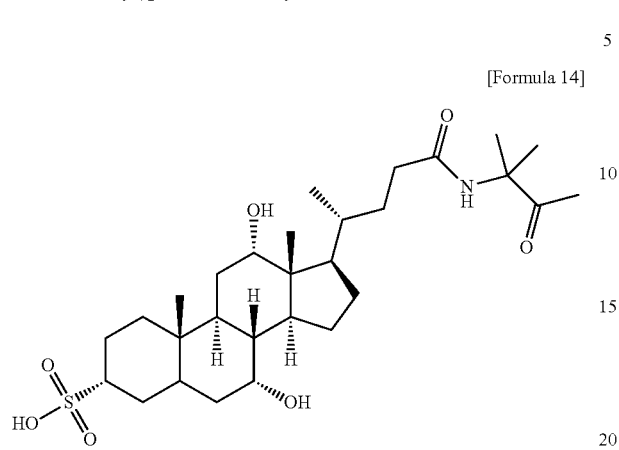

3R,7R,8R,9S,10S,12S,13R,14S,17R)-7,12-dihydroxy-10,
13-dimethyl-17-((R)-5-((2-methyl-3-oxobutan-2-yl)
amino)-5-oxopentan-2-yl)hexadecahydro-1H-cyclopenta
[a]phenanthrene-3-sulfonic acid

[Formula 15]

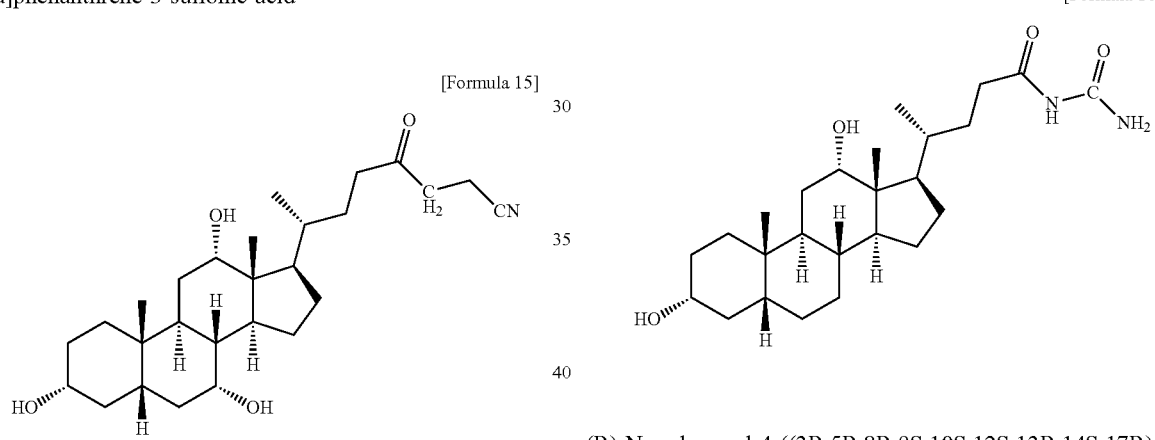

(R)-4-oxo-7-((3R,5S,7R,8R,9S,10S,12S,13R,14S,17R)-3,7,
12-trihydroxy-10,13-dimethylhexadecahydro-1H-cyclo-
penta[a]phenanthren-17-yl)octanenitrile

[Formula 16]

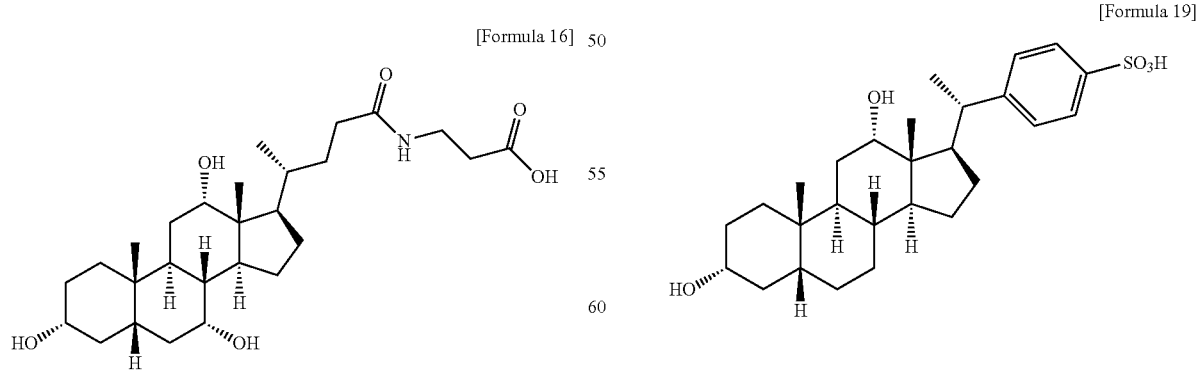

3-((R)-4-((3R,5S,7R,8R,9S,10S,12S,13R,14S,17R)-3,7,12-
trihydroxy-10,13-dimethylhexadecahydro-1H-cyclopenta
[a]phenanthren-17-yl)pentanamido)propanoic acid

[Formula 17]

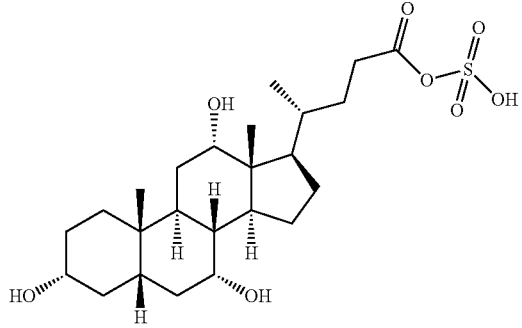

(R)-4-((3R,5S,7R,8R,9S,10S,12S,13R,14S,17R)-3,7,12-tri-
hydroxy-10,13-dimethylhexadecahydro-1H-cyclopenta
[a]phenanthren-17-yl)pentanoic sulfuric anhydride

[Formula 18]

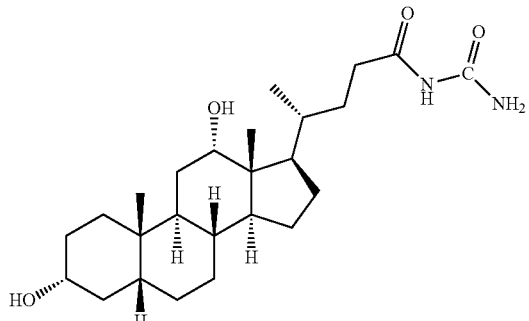

(R)-N-carbamoyl-4-((3R,5R,8R,9S,10S,12S,13R,14S,17R)-
3,12-dihydroxy-10,13-dimethylhexadecahydro-1H-cy-
clopenta[a]phenanthren-17-yl)pentanamide

[Formula 19]

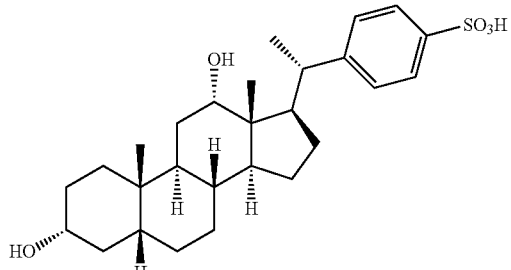

4-((S)-1-((3R,5R,8R,9S,10S,12S,13S,14S,17R)-3,12-dihy-
droxy-10,13-dimethylhexadecahydro-1H-cyclopenta[a]
phenanthren-17-yl)ethyl)benzenesulfonic acid

[Formula 20]

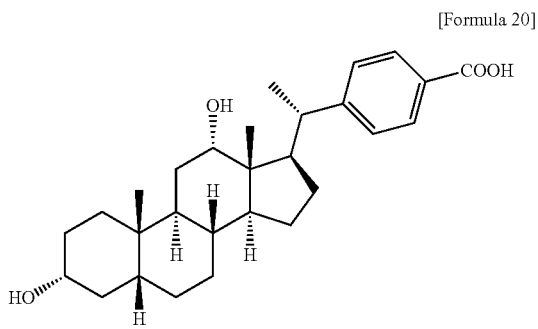

4-((S)-1-((3R,5R,8R,9S,10S,12S,13S,14S,17R)-3,12-dihydroxy-10,13-dimethylhexadecahydro-1H-cyclopenta[a]phenanthren-17-yl)ethyl)benzoic acid The bile acid includes an α-face exhibiting hydrophilicity since at least one —OH and a —COOH or —SO$_3$H group are exposed, and a β-face exhibiting hydrophobicity since —CH$_3$ groups are exposed, thereby exhibiting amphiphilicity. Also, the bile acid derivative includes an α-face exhibiting hydrophilicity since G$_1$ groups of Formula 3 are exposed and a β-face exhibiting hydrophobicity since —CH$_3$ groups are exposed, resulting in exhibiting amphiphilicity.

The bacteriophage is known to include a protein part and hydrophobic tails. Therefore, the bacteriophage may be amphiphilic. The bacteriophage may be a rod-shaped filamentous bacteriophage. The filamentous bacteriophage is known to have a hydrophilic rod disposed in the center due to a residue such as a carboxyl group or amine group, and hydrophobic tails disposed at both ends. In one example, the bacteriophage may be at least one selected from the group consisting of T1, T2, T3, T4, T5, T6, T7, M13, MS2, fd, f1 and P22.

The hydrophilic portion 10a of such an amphiphilic substance 10 may be bound to edges having high surface energy, particularly, an edge having the highest surface energy, of the two-dimensional material 30. Specifically, an edge of the two-dimensional material 30 may be bound to the hydrophilic portion 10a of the amphiphilic substance 10 by a surface interaction 21. The surface interaction may be a hydrophilic-hydrophilic interaction, an interaction between a Lewis acid and a Lewis base, or a hydrogen bond. Here, the hydrophobic portions 10b of the amphiphilic substances 10, wherein the amphiphilic substances 10 are adjacent to each other and bound to the edges of the two-dimensional material 30, may be bound to each other by a force 22 such as a van der Waals force. Therefore, the amphiphilic substance 10 may be self-assembled to the edge of the two-dimensional material 30.

Referring to both FIGS. 1 and 2, the hydrophobic portions 10b of the self-assembled amphiphilic substance 10 may have an interaction 23 with an in-plane region of the two-dimensional material 30 by van der Waals forces 23. Such an interaction may initiate scrolling of the two-dimensional material 30. However, even when there is no interaction 23, it is assumed that the scrolling of the two-dimensional material 30 may be initiated only by the surface interactions 21 between the edge of the two-dimensional material 30 and the hydrophilic portions 10a of the amphiphilic substance 10.

Once the scrolling of the two-dimensional material 30 is initiated, the scrolling is accelerated by van der Waals interactions 25, for example, a π-π interaction, between in-plane regions of the two-dimensional material 30, and thus the two-dimensional material 30 may be changed into a scrolled structure, that is, a roll shape. As a result, a scroll composite 40, in which the amphiphilic substance 10 is disposed inside, specifically, in the center of the scrolled structure of the two-dimensional material, may be formed. The two-dimensional material scroll, that is, the scroll composite 40 may have a one-dimensional structure, which is rod shaped or fiber shaped, and have open ends.

The amphiphilic substance 10 may remain in the scroll composite 40. As the size, shape or amount of the amphiphilic substance 10 is adjusted, the inner size of the scroll composite 40 is able to be adjusted.

Referring to FIG. 3, as at least a part or all of the amphiphilic substance 10 may be removed from the scroll composite 40 using solvent treatment and/or thermal treatment, a hollow scroll 50 that is empty at least in a part or throughout may be prepared. The hollow scroll 50 may have a one-dimensional structure, that is, a hollow rod-shaped or fiber-shaped structure, that is, a tube-shaped structure. However, the hollow scroll 50 may have a structure with open ends, unlike a carbon nanotube.

Etching may be enhanced by adding thermal treatment while using the solvent.

The solvent, which is a material capable of selectively dissolving only the amphiphilic substance 10, may be at least one selected from the group consisting of water, methanol, ethanol, isopropyl alcohol, toluene, benzene, hexane, heptane, m-cresol, ethyl acetate, carbon disulfide, dimethylsulfoxide, dichloromethane, dichlorobenzene, chloroform, carbon tetrachloride, acetone, tetrahydrofuran, dimethylacctamide, N-methylpyrrolidone, dimethylformamide and acetic acid, and a solvent treatment time may be 1 to 24 hours, or several days, but the present invention is not limited thereto.

Meanwhile, the scroll composite may not be unrolled in the solvent by the van der Waals interactions 25 between adjacent two-dimensional material sheets.

To the extent that a shape of the scroll is not deformed, a temperature of the thermal treatment may be, but is not particularly limited to, for example, 100 to 800° C., 100 to 700° C., 100 to 600° C., 100 to 500° C., 200 to 800° C., 200 to 700° C., 200 to 600° C., 200 to 500° C., 300 to 800° C., 300 to 700° C., 300 to 600° C., 300 to 500° C., 400 to 800° C., 400 to 700° C., 400 to 600° C., or 400 to 500° C., 500 to 800° C., 500 to 700° C., or 500 to 600° C., the treatment time may be, but is not limited to, 0.1 to 10 hours. When the thermal treatment is performed in a gas atmosphere, a gas may be, for example, argon, nitrogen, etc. Also, the inert gas may be provided at a rate of, for example, approximately 1 to 10 cc/min.

The thermal treatment may be, but is not limited to, induction heating, radiant heat, laser, IR, microwave, plasma, UV or surface plasmon heating.

FIG. 4 is the schematic diagram illustrating a method for preparing a scroll according to another exemplary embodiment of the present invention. Except the following description, the method for preparing a scroll according to this exemplary embodiment may be similar to that described with reference to FIGS. 1 to 3. Also, FIG. 4 is the diagram of an enlarged edge of the two-dimensional material.

Referring to FIG. 4, a filamentous bacteriophage may be provided on a two-dimensional material 30 as an amphiphilic substance 10. It is known that the filamentous bacteriophage, as described with reference to FIG. 1, has a hydrophilic rod 10a disposed in the center due to a residue such as a carboxyl group or amine group, and hydrophobic tails 10b disposed at both ends. In one example, the bacteriophage may be at least one selected from the group consisting of T1, T2, T3, T4, T5, T6, T7, M13, MS2, fd, f1 and P22.

The hydrophilic rod 10a of such a bacteriophage 10 may be bound to edges having high surface energy, particularly, an edge having the highest surface energy among these edges, of the two-dimensional material 30. Specifically, an edge of the two-dimensional material 30 may be bound to the hydrophilic rod 10a of the bacteriophage 10 by a surface interaction 21. The hydrophobic tails 10b of the bacteriophage 10 may have an interaction 23 with an in-plane region of the two-dimensional material 30 by van der Waals forces. Such an interaction may initiate scrolling of the two-dimensional material 30. However, even when there is no such interaction 23, it is assumed that the scrolling of the two-dimensional material 30 may be initiated only by the surface interaction 21 between an edge of the two-dimensional material 30 and the hydrophilic rod 10a of the bacteriophage 10. After the scrolling of the two-dimensional material 30 is initiated, the scrolling is accelerated by the van der Waals interactions 25 (FIG. 2) between the in-plane regions of the two-dimensional material 30, thereby forming a scroll composite 40 (FIG. 2). Also, afterward, the bacteriophage may be removed using a solvent for selective lysis or etching, thereby forming a hollow scroll 50 (FIG. 3).

FIGS. 5, 6, and 7 are the schematic diagrams illustrating a method for preparing a scroll according to still another exemplary embodiment of the present invention. Except the following description, the method for preparing a scroll according to this exemplary embodiment may be similar to that described with reference to FIGS. 1 to 3. Also, FIGS. 5 and 6 show the enlarged edges of a two-dimensional material.

Referring to FIGS. 5 and 6, self assemblies M1 and M2 of an amphiphilic substance may be provided on the two-dimensional material 30. To this end, the concentration of the amphiphilic substance 10 in an amphiphilic substance solution prepared by dissolving the amphiphilic substance 10 in a solvent may be adjusted to a critical micelle concentration or higher, and before being mixed with a two-dimensional material dispersion, the amphiphilic substance solution may be heated to a predetermined temperature, cooled, and then maintained for predetermined time. In this process, the amphiphilic substance 10 is self-assembled in the amphiphilic substance solution, and thus may form a rod-shaped or fiber-shaped self assembly M1 as shown in FIG. 5, or a spherical self assembly M2 as shown in FIG. 6. The self assemblies M1 and M2 may also be called micelles.

In such self assemblies M1 and M2, hydrophilic portions 10a of the amphiphilic substance 10 may be exposed to the outside. Meanwhile, the shape of such self assemblies M1 and M2 may be determined by a solvent in the amphiphilic substance solution.

Meanwhile, the diameter and/or length of the self assemblies M1 and M2 may be changed depending on the concentration, heating temperature, cooling temperature, and maintaining time of the amphiphilic substance in the amphiphilic substance solution. To this end, the concentration of the amphiphilic substance in the amphiphilic substance solution may be approximately 0.001 g/L to 1 g/L. The heating temperature may be 30 to 200° C. The cooling temperature may be approximately −196 to 25° C. Also, the maintaining time may be 0.5 to 24 hours.

FIGS. 5 and 6 show that the self assemblies M1 and M2 are formed to have a monolayer shell of the amphiphilic substance 10, but the present invention is not limited thereto. In FIGS. 8 and 9, self assemblies M1 and M2 are formed with a multi-layered shell of the amphiphilic substance 10, and the diameters of the assemblies may be adjusted by the number of the shell layers.

The hydrophilic portions 10a of the amphiphilic substance, which are exposed to the outside, of such self assemblies M1 and M2 may be bound to edges of the two-dimensional material 30 having high surface energy, particularly, an edge having the highest surface energy. Specifically, an edge of the two-dimensional material 30 may be bound to the hydrophilic portions 10a of the amphiphilic substance 10 by surface interactions 21. Meanwhile, the hydrophobic portions 10b of the amphiphilic substance 10 may be exposed in a region of the self assemblies M1 and M2, in which the amphiphilic substance 10 is disposed at a very low density, and the exposed hydrophobic portions 10b may have interactions 23 with an in-plane region of the two-dimensional material 30 by van der Waals forces. Such interactions may initiate scrolling of the two-dimensional material 30. However, even when there is no interaction 23, it is assumed that the scrolling of the two-dimensional material 30 may be initiated only by the surface interactions 21 between an edge of the two-dimensional material 30 and the hydrophilic portions 10a of the amphiphilic substance 10.

Referring to FIG. 7, after the scrolling of the two-dimensional material 30 is initiated, the scrolling is accelerated by van der Waals interactions 25 between the in-plane regions of the two-dimensional material 30, and thus a scroll composite 40 may be formed. Since the amphiphilic substance 10 forms the self assemblies M1 and M2, the scroll composite 40 according to the this exemplary embodiment may have a larger inner diameter than that described with reference to FIG. 2.

Afterward, a hollow scroll 50 (of FIG. 3) may be prepared by removing the amphiphilic substance 10 from the scroll composite 40 using a solvent and/or thermal treatment. However, the hollow scroll formed in this exemplary embodiment may have a larger inner diameter than that described with reference to FIG. 3.

FIGS. 8 and 9 are the schematic diagrams illustrating methods for preparing a scroll according to yet another exemplary embodiment of the present invention. Except the following description, the method for preparing a scroll according to this exemplary embodiment may be similar to that described with reference to FIGS. 1 to 3. Also, FIGS. 8 and 9 show an enlarged edge of a two-dimensional material.

Referring to FIGS. 8 and 9, self assemblies C1 and C2 of an amphiphilic substance may be provided on a two-dimensional material 30. The self assemblies C1 and C2 of the amphiphilic substance may be formed by self-assembling the amphiphilic substance 10 on core particles 15 and 17. The core particles 15 and 17 may be metal particles, metal oxide particles, or bacteriophages, and as shown in FIG. 9, spherical particles 15, or as shown in FIG. 8, rod-shaped particles 17. The bacteriophages may correspond to the rod-shaped particles 17, as shown in FIG. 8. When the amphiphilic substance 10 is self-assembled on the spherical particle 15, the self assembly C1 of the amphiphilic substance may have a spherical shape, and however, when amphiphilic substance 10 is self-assembled on the rod-shaped particle 17, the self assembly C2 of the amphiphilic substances may have a rod or fiber shape.

The metal particles may be Au, Ag, Fe, Al, Cu, Co, Ni, W, Zn, Mo, Ti, Ru, Pd, Ge, Pt, Li, Si, or an alloy particle of two or more thereof, and may have a diameter of 1 nm to 10 μm. The metal oxide particles may be $Al(OH)_3$, $Al_2O_3$, $MnO$, $SiO_2$, $ZnO$, $Fe_2O_3$, $Fe_3O_4$, $Li_4Ti_5O_{12}$, $LiNi_{0.5}Mn_{1.5}O_4$ or TiO$_2$ particles, and may have a diameter of 1 nm to 10 µm. When the metal particles or metal oxide particles have a rod shape, the particle may have a length of 1 nm to 10 µm.

The providing of the self assemblies C1 and C2 of the amphiphilic substance on the two-dimensional material 30 may be performed by stirring the amphiphilic substance 10 and the core particles added to a solvent, thereby preparing an amphiphilic substance solution, and mixing the amphiphilic substance solution with a two-dimensional material dispersion.

The metal particles, the metal oxide particles, and the bacteriophages 15 and 17 may have a hydrophilic surface, and thus hydrophilic portions 10a of the amphiphilic substance 10 may be self-assembled on the hydrophilic substance, thereby forming a first shell S1. On the surface of the first shell S1, hydrophobic portions 10b of the amphiphilic substance 10 may be exposed, and hydrophobic portions 10b of the amphiphilic substance 10 may be self-assembled again on the surface of the first shell S1, thereby forming a second shell S2. The hydrophilic portion 10a may be exposed at the surface of the second shell S2. However, since the second shell S2 may have the amphiphilic substance 10 disposed at a very low density, compared with the first shell S1, both of the hydrophilic portion 10a and the hydrophobic portion 10b may be exposed to the surfaces of the self assemblies C1 and C2 of the amphiphilic substance.

The hydrophilic portion 10a exposed at the surface of the self assemblies C1 and C2 of the amphiphilic substance may be bound to edges of the two-dimensional material 30 having high surface energy, particularly, an edge having the highest surface energy. Further, the hydrophobic portions 10b exposed at the surfaces of the self assemblies C1 and C2 of the amphiphilic substance may have interactions 23 with an in-plane region of the two-dimensional material 30 by van der Waals forces. Such an interaction may initiate scrolling of the two-dimensional material 30. However, even when there is no such interaction 23, it is assumed that the scrolling of the two-dimensional material 30 may be initiated only by surface interactions 21 between an edge of the two-dimensional material 30 and the hydrophilic portions 10a of the amphiphilic substances 10.

After the scrolling of the two-dimensional material 30 is initiated, the scrolling is accelerated by van der Waals interactions 25 (of FIG. 2) between the in-plane regions of the two-dimensional material 30, thereby forming a scroll composite 40 (of FIG. 2). However, as the self assemblies C1 and C2 are formed of the amphiphilic substance 10 along with the particles 15 and 17, the scroll composite according to the exemplary embodiment may have a larger inner diameter than that described with reference to FIG. 2.

In addition, the inner size, for example, the inner diameter of the scroll composite 40 (of FIG. 2) is able to be adjusted by adjusting the size, for example, the diameters of the self assemblies C1 and C2 of the amphiphilic substance. The size of the self assemblies C1 and C2 of the amphiphilic substance may be adjusted depending on the size of the particles 15 and 17 and/or the number of layers of the shells S1 and S2 composed of the amphiphilic substance 10.

Afterward, a hollow scroll 50 (of FIG. 3) may be prepared by removing the amphiphilic substance 10 from the scroll composite using a solvent and/or thermal treatment. Here, when the amphiphilic substance 10 having an interaction with the two-dimensional material 30 is removed, the core particle may also be removed. However, the hollow scroll formed in the exemplary embodiment may have a larger inner diameter than that described with reference to FIG. 3.

Hereinafter, exemplary examples are provided to help in understanding the present invention. However, the following examples are merely provided to help in understanding the present invention, not to limit the present invention by the following examples.

Preparation Examples 1 to 13, 66 to 68

1.5 g of graphene, which is a two-dimensional material, was put into a solvent shown in Table 2 or 6, and dispersed by mechanical stirring at 2400 rpm for 1 hour. Afterward, following sonication for 30 minutes, the dispersion was centrifuged at 4400 rpm for 30 minutes, thereby obtaining a graphene dispersion, which is a supernatant.

Meanwhile, any one of the amphiphilic substances such as bile acid derivatives represented by Formulas 4 to 8 (Preparation Examples 1 to 6), sodium dodecyl sulfate (Preparation Example 7), lauroyl microgol glyceride (Preparation Example 8), sodium cholate hydrate as a hydrate of a bile acid salt (Preparation Example 9), deoxycholic acid as bile acid (Preparation Example 9), bacteriophages T1, M13, and fd (Preparation Examples 11 to 13), or bile acid derivatives represented by Formulas 13 to 15 (Preparation Examples 66 to 68) was put into a solvent shown in Table 2 or 6 with a weight shown in Table 2 or 6, thereby preparing an amphiphilic substance solution. Afterward, the resulting solution was heated to a temperature shown in Table 2 or 6.

Afterward, in Preparation Examples 2 to 4, 6 to 8, 10 to 13, and 66, the amphiphilic substance solution may be maintained at a temperature shown in Table 2 or 6 for a time shown in Table 2 or 6 to recrystallize, self-assemble or micellize the amphiphilic substance.

After the graphene dispersion was mixed with the amphiphilic substance solution, the resulting mixed solution was maintained at a temperature shown in Table 2 or 6 for a time shown in Table 2 or 6. Afterward, graphene scroll composites including the amphiphilic substance inside a graphene scroll were obtained by filtering with a PTFE membrane.

Preparation Example 14

A graphene dispersion was obtained using the same method as described in Preparation Example 1, except that 1.5 g of graphene was put into methanol.

A bile acid derivative (Formula 4) as an amphiphilic substance, and TiO$_2$ particles (diameter: 20 nm, R&D Korea) as metal oxide particles were added to methanol in a weight ratio of 97:3, thereby preparing a solution having a sum concentration of 2.0 wt %, and the resulting solution was stirred for 5 hours, resulting in an amphiphilic substance solution. Afterward, the amphiphilic substance solution was heated to 65° C., and maintained at 11° C. for 3 hours.

Subsequently, the graphene dispersion was mixed with the amphiphilic substance solution, and then the resulting mixture was maintained at 60° C. for 5 hours. As a result, a graphene scroll composite including a self assembly of the amphiphilic substance inside a graphene scroll was obtained.

Preparation Example 15

A graphene dispersion was obtained using the same method as described in Preparation Example 1, except that 1.5 g of graphene was added to heptane.

A bile acid derivative of Formula 4 as an amphiphilic substance and a bacteriophage P22 were added to heptane in a weight ratio of 80:20, thereby preparing a solution having a sum concentration of 3.0 wt %, and the resulting solution was stirred for 1 hour, resulting in an amphiphilic substance solution. Afterward, the amphiphilic substance solution was heated to 90° C.

The graphene dispersion was mixed with the amphiphilic substance solution, and then maintained at 180° C. for 3 hours. As a result, a graphene scroll composite including a self assembly of the amphiphilic substance inside a graphene scroll was obtained.

Preparation Example 16

A graphene dispersion was obtained using the same method as described in Preparation Example 1, except that 1.5 g of graphene was added to carbon disulfide.

Deoxycholic acid as an amphiphilic substance and a $Fe_3O_4$ particles as metal oxide particles were added to carbon disulfide in a weight ratio of 60:40, thereby preparing a solution having a sum concentration of 5 wt %, and the resulting solution was stirred for 3 hours, resulting in an amphiphilic substance solution. Afterward, the amphiphilic substance solution was heated to 110° C., and maintained at 0° C. for 4 hours.

The graphene dispersion was mixed with the amphiphilic substance solution, and maintained at 10° C. for 6 hours. As a result, a graphene scroll composite including a self assembly of the amphiphilic substance inside a graphene scroll was obtained.

Preparation Example 17

A graphene dispersion was obtained using the same method as described in Preparation Example 1, except that 1.5 g of graphene was added to dichloromethane.

A sodium dodecyl sulfate as an amphiphilic substance and Ag particles (diameter: 1 μm, R&D Korea) as metal particles were added to dichloromethane in a weight ratio of 90:10, thereby preparing a solution having a sum concentration of 2.0 wt %, and the resulting solution was stirred for 1 hour, resulting in an amphiphilic substance solution. Afterward, the amphiphilic substance solution was heated to 40° C., and maintained at −4° C. for 5.5 hours.

The graphene dispersion was mixed with the amphiphilic substance solution, and maintained at room temperature for 1 hour. As a result, a graphene scroll composite including a self assembly of the amphiphilic substance inside a graphene scroll was obtained.

Preparation Example 18

1.5 g of boron nitride as a two-dimensional material was added to 5 ml of ODCB, and dispersed by mechanical stirring at 2400 rpm for 1 hour. Afterward, following sonication for 30 minutes and centrifugation at 4400 rpm for 30 minutes, a boron nitride dispersion, which is a supernatant, was obtained.

Meanwhile, 0.02 mmol of the bile acid derivative of Formula 4 as an amphiphilic substance was dissolved in 1 ml of ODCB, thereby preparing an amphiphilic substance solution. The amphiphilic substance solution was heated to 60° C.

The boron nitride dispersion was mixed with the heated amphiphilic substance solution, and maintained at room temperature for 24 hours. As a result, a boron nitride dispersion scroll composite including a self assembly of the amphiphilic substance inside a boron nitride dispersion scroll was obtained.

Preparation Example 19

0.002 mmol of the bile acid derivative of Formula 4 as an amphiphilic substance was dissolved in 1 ml of ODCB, thereby preparing an amphiphilic substance solution. The amphiphilic substance solution was heated to 60° C. Afterward, the heated amphiphilic substance solution was maintained at room temperature for 24 hours. Except the above-described process, a boron nitride scroll composite including the amphiphilic substance inside a boron nitride scroll was obtained using the same method as used in Preparation Example 18.

Preparation Examples 20 to 32, 69, and 70

1.5 g of boron nitride as a two-dimensional material was added to a solvent shown in Table 3 or 6, and dispersed by mechanical stirring at 2400 rpm for 1 hour. Afterward, following sonication for 30 minutes and centrifugation at 4400 rpm for 30 minutes, a boron nitride dispersion as a supernatant was obtained.

Meanwhile, any one of the amphiphilic substances such as an N-hexadecyltrimethylammonium salt (Preparation Example 20), benzalkonium chloride (Preparation Example 21), a bile acid derivative represented by Formula 7 (Preparation Example 22), a bile acid derivative represented by Formula 8 (Preparation Example 23), sodium dodecylsulfate (Preparation Example 24), sodium laureth sulfate (Preparation Example 25), cetylpyridinium chloride (CPCl) (Preparation Example 26), α-tocopherol as a synthetic vitamin E derivative (Preparation Example 27), sodium taurocholate (Preparation Example 28), bacteriophages M13, fd, T2, and MS2 (Preparation Examples 29 to 32), or bile acid derivatives represented by Formulas 16 and 17 (Preparation Examples 69 and 70) was dissolved in a solvent shown in Table 3 or 6 with a weight shown in Table 3 or 6, thereby preparing an amphiphilic substance solution. Afterward, the resulting solution was heated to a temperature shown in Table 3 or 6.

Afterward, in Preparation Examples 21, 23 to 27, 29 to 32, 69, and 70, the amphiphilic substance solution was maintained at a temperature shown in Table 3 or 6 for a time shown in Table 3 or 6 to recrystallize, self-assemble or micellize the amphiphilic substance.

The boron nitride dispersion was mixed with the amphiphilic substance solution, and maintained at a temperature shown in Table 3 or 6 for a time shown in Table 3 or 6. As a result, boron nitride scroll composites including an amphiphilic substance inside a boron nitride scroll were obtained.

Preparation Examples 33 to 47, 71 to 73

1.5 g of molybdenum sulfide as a two-dimensional material was added to a solvent shown in Table 4 or 6, and dispersed by mechanical stirring at 2400 rpm for 1 hour. Afterward, following sonication for 30 minutes and centrifugation at 4400 rpm for 30 minutes, a molybdenum sulfide dispersion as a supernatant was obtained.

Meanwhile, any one of the amphiphilic substances such as cetyl alcohol (Preparation Example 33), polyoxyethylene-polyoxypropylene (Preparation Example 34), lauroyl microgol glyceride (Preparation Example 35), sodium cholate hydrate (Preparation Example 36), deoxycholic acid (Preparation Example 37), bile acid derivatives represented by Formulas 4 to 8 (Preparation Examples 38 to 42), bacteriophages T2, T4, M13, fd, and P22 (Preparation Examples 43 to 47), and bile acid derivatives represented by Formulas 18 to 20 (Preparation Examples 71 to 73) was dissolved in a solvent shown in Table 4 or 6 with a weight shown in Table 4 or 6, thereby preparing an amphiphilic substance solution. Afterward, the resulting solution was heated to a temperature shown in Table 4 or 6.

Subsequently, in Preparation Examples 34, 35, 38 to 45, and 73, the amphiphilic substance solution was maintained at a temperature shown in Table 4 or 6 for a time shown in table 4 or 6 to recrystallize, self-assemble or micellize the amphiphilic substance.

The molybdenum sulfide dispersion was mixed with the amphiphilic substance solution, and maintained at a temperature shown in Table 4 or 6 for a time shown in Table 4 or 6. As a result, molybdenum sulfide scroll composites including the amphiphilic substance inside a molybdenum sulfide scroll were obtained.

Preparation Example 48

A molybdenum sulfide dispersion was obtained using the same method as used in Preparation Example 47, except that 1.5 g of molybdenum sulfide was added to dichloromethane.

A bile acid derivative of Formula 7 as an amphiphilic substance and a bacteriophage fd were added to dichloromethane in a weight ratio of 70:30, thereby preparing a solution having a sum concentration of 6 wt %, and the resulting solution was stirred for 0.5 hours, resulting in an amphiphilic substance solution. Afterward, the amphiphilic substance solution was heated to 55° C.

The molybdenum sulfide dispersion was mixed with the amphiphilic substance solution, and maintained at room temperature for 24 hours. As a result, a molybdenum sulfide scroll composite including a self assembly of the amphiphilic substance inside a molybdenum sulfide scroll was obtained.

Preparation Example 49

A molybdenum sulfide dispersion was obtained using the same method as used in Preparation Example 47, except that 1.5 g of molybdenum sulfide was added to ODCB.

Cetyl alcohol as an amphiphilic substance and a bacteriophage P22 were added to ODCB in a weight ratio of 50:50, thereby preparing a solution having a sum concentration of 5 wt %, and the resulting solution was stirred for 3 hours, resulting in an amphiphilic substance solution. Afterward, the amphiphilic substance solution was heated to 120° C.

The molybdenum sulfide dispersion was mixed with the amphiphilic substance solution, and maintained at 100° C. for 11 hours. As a result, a molybdenum sulfide scroll composite including a self assembly of the amphiphilic substance inside a molybdenum sulfide scroll was obtained.

Preparation Example 50

A molybdenum sulfide dispersion was obtained using the same method as used in Preparation Example 47, except that 1.5 g of molybdenum sulfide was added to chloroform.

An N-hexadecyltrimethylammonium salt as an amphiphilic substance and $Al(OH)_3$ particles as metal oxide particles were added to chloroform in a weight ratio of 70:30, thereby preparing a solution having a sum concentration of 2 wt %, and the resulting solution was stirred for 1 hour, resulting in an amphiphilic substance solution. Afterward, the amphiphilic substance solution was heated to 40° C., and maintained at room temperature for 18 hours.

The molybdenum sulfide dispersion was mixed with the amphiphilic substance solution, and maintained at room temperature for 0.1 hours. As a result, a molybdenum sulfide scroll composite including a self assembly of the amphiphilic substance inside a molybdenum sulfide scroll was obtained.

Preparation Example 51

A molybdenum sulfide dispersion was obtained using the same method as used in Preparation Example 47, except that 1.5 g of molybdenum sulfide was added to acetic acid.

Sodium dodecylsulfate as an amphiphilic substance and $SiO_2$ particles as metal oxide particles were added to acetic acid in a weight ratio of 95:5, thereby preparing a solution having a sum concentration of 1 wt %, and the resulting solution was stirred for 4 hours, resulting in an amphiphilic substance solution. Afterward, the amphiphilic substance solution was heated to 70° C., and maintained at −60° C. for 2 hours.

The molybdenum sulfide dispersion was mixed with the amphiphilic substance solution, and maintained at 250° C. for 0.5 hours. As a result, a molybdenum sulfide scroll composite including a self assembly of the amphiphilic substance inside a molybdenum sulfide scroll was obtained.

Preparation Examples 52 to 59

1.5 g of graphene/boron carbon nitride (BCN) as a two-dimensional material was added into a solvent shown in Table 5, and dispersed by mechanical stirring at 2400 rpm for 1 hour. Afterward, following sonication for 30 minutes and centrifugation at 4400 rpm for 30 minutes, a graphene/boron carbon nitride dispersion as a supernatant was obtained.

Meanwhile, any one of the amphiphilic substances such as sodium laureth sulfate (Preparation Example 52), cetylpyridinium chloride (CPCl) (Preparation Example 53), α-tocopherol as a synthetic vitamin E derivative (Preparation Example 54), sodium taurocholate (Preparation Example 55), and bacteriophages M13, fd, T2, and MS2 (Preparation Examples 56 to 59) was dissolved in a solvent shown in Table 5 with a weight shown in Table 5, thereby preparing an amphiphilic substance solution. Afterward, the resulting solution was heated to a temperature shown in Table 5.

Subsequently, in Preparation Examples 52 to 55, 58, and 59, the amphiphilic substance solution was maintained at a temperature shown in Table 5 and for a time shown in Table 5 to recrystallize, self-assemble or micellize the amphiphilic substance.

The graphene/boron carbon nitride dispersion was mixed with the amphiphilic substance solution, and maintained at a temperature shown in Table 5 and for a time shown in Table 5. As a result, graphene/boron carbon nitride scroll composite materials including an amphiphilic substance inside a graphene/boron carbon nitride scroll were obtained.

Preparation Examples 60 to 65

1.5 g of graphene/molybdenum sulfide as a two-dimensional material was added to a solvent shown in Table 5, and dispersed by mechanical stirring at 2400 rpm for 1 hour. Afterward, the sonication for 30 minutes and centrifugation at 4400 rpm for 30 minutes, a graphene/molybdenum sulfide dispersion as a supernatant was obtained.

Meanwhile, any one of the amphiphilic substances such as bile acid derivatives represented by Formulas 5 to 8 (Preparation Examples 60 to 63), sodium dodecyl sulfate (Preparation Example 64), and lauryloyl microgol glyceride (Preparation Example 65) was dissolved in a solvent shown in Table 5 with a weight shown in Table 5, thereby preparing an amphiphilic substance solution. Afterward, the resulting solution was heated at a temperature shown in Table 5.

Subsequently, in Preparation Examples 60, 63, and 64, the amphiphilic substance solution was maintained at a temperature shown in Table 5 and for a time shown in Table 5 to recrystallize, self-assemble or micellize the amphiphilic substance.

The graphene/molybdenum sulfide dispersion was mixed with the amphiphilic substance solution, and maintained at a temperature shown in Table 5 for a time shown in Table 5. As a result, graphene/molybdenum sulfide scroll composites including an amphiphilic substance inside a graphene/molybdenum sulfide scroll were obtained.

TABLE 2

| | Two-dimensional material dispersion | | | Amphiphilic substance solution | | | Maintenance condition for amphiphilic substance solution | | Mixed solution | |
|---|---|---|---|---|---|---|---|---|---|---|
| Preparation Example | two-dimensional material (1.5 g) | solvent (volume) | temperature (° C.) | amphiphilic substance (mole number or weight) | solvent (volume) | heating temperature | temperature (° C.) | maintenance time (hr) | temperature (° C.) | maintenance time (hr) |
| Preparation Example 1 | graphene | ODCB (5 ml) | room temperature (R.T.) | bile acid derivative (Formula4) (0.02 mmol) | ODCB (1 ml) | 60° C. | — | — | R.T. | 24 |
| Preparation Example 2 | graphene | ODCB (5 ml) | R.T. | bile acid derivative (Formula4) (0.02 mmol) | ODCB (1 ml) | 60 | R.T. | 24 | R.T. | 24 |
| Preparation Example 3 | graphene | toluene (5 ml) | 60° C. | bile acid derivative (Formula5) (0.02 mmol) | toluene (1 ml) | 180° C. | 18° C. | 0.5 | 60° C. | 4 |
| Preparation Example 4 | graphene | isopropyl alcohol (500 ml) | 60° C. | bile acid derivative (Formula6) (0.2 mmol) | Isopropyl alcohol (100 ml) | 100° C. | −196° C. | 0.5 | 180° C. | 0.1 |
| Preparation Example 5 | graphene | benzene (5 ml) | 70° C. | bile acid derivative (Formula 7) (0.01 g) | benzene (5 ml) | 100° C. | — | — | 10° C. | 12 |
| Preparation Example 6 | graphene | tetrahydrofuran (15 ml) | R.T. | bile acid derivative (Formula 8) (0.1 g) | tetrahydrofuran (5 ml) | 70° C. | 4° C. | 4 | R.T. | 3 |
| Preparation Example 7 | graphene | ODCB (15 ml) | R.T. | sodium dodecylsulfate (0.05 g) | ODCB (2 ml) | 180° C. | 0° C. | 0.1 | 200° C. | 5 |
| Preparation Example 8 | graphene | carbon tetrachloride (5 ml) | 65° C. | lauryloyl microgol glyceride (0.01 g) | carbon tetrachloride (1 ml) | 200° C. | −10° C. | 12 | 300° C. | 7 |
| Preparation Example 9 | graphene | ODCB (5 ml) | 90° C. | sodium cholate hydrate (0.01 g) | ODCB (1 ml) | 300° C. | — | — | R.T. | 10 |
| Preparation Example 10 | graphene | chloroform (500 ml) | 55° C. | deoxycholic acid (0.1 g) | chloroform (100 ml) | 60° C. | 0° C. | 5 | 100° C. | 24 |
| Preparation Example 11 | graphene | acetic acid (50 ml) | 65° C. | T1 (0.02 g) | acetic acid (1 ml) | 100° C. | 4° C. | 7 | R.T. | 0.5 |
| Preparation Example 12 | graphene | ODCB (25 ml) | 90° C. | M13 (0.01 g) | ODCB (15 ml) | 30° C. | 18° C. | 10 | 250° C. | 2 |
| Preparation Example 13 | graphene | water (15 ml) | 40° C. | fd (0.001 g) | water (10 ml) | 200° C. | 13° C. | 24 | 120° C. | 2 |
| Preparation Example 14 | graphene | methanol (20 ml) | 40° C. | $TiO_2$/bile acid derivative (Formula4) (0.05 g) | methanol (10 ml) | 65° C. | 11° C. | 3 | 60° C. | 5 |

TABLE 2-continued

| Preparation Example | Two-dimensional material dispersion | | | Amphiphilic substance solution | | | Maintenance condition for amphiphilic substance solution | | Mixed solution | |
|---|---|---|---|---|---|---|---|---|---|---|
| | two-dimensional material (1.5 g) | solvent (volume) | temperature (° C.) | amphiphilic substance (mole number or weight) | solvent (volume) | heating temperature | temperature (° C.) | maintenance time (hr) | temperature (° C.) | maintenance time (hr) |
| Preparation Example 15 | graphene | heptane (30 ml) | R.T. | P22/ bile acid derivative (Formula 4) (0.05 g) | heptane (10 ml) | 90° C. | — | — | 180° C. | 3 |
| Preparation Example 16 | graphene | carbon disulfide (35 ml) | 55° C. | Fe3O4/ deoxycholic acid (0.03 g) | carbon disulfide (15 ml) | 110° C. | 0° C. | 4 | 10° C. | 6 |
| Preparation Example 17 | graphene | dichloromethane (55 ml) | 65° C. | Ag/ sodium dodecyl sulfate (0.01 g) | dichloromethane (10 ml) | 40° C. | −4° C. | 5.5 | R.T. | 1 |

TABLE 3

| Preparation Example | Two-dimensional material dispersion | | | Amphiphilic substance solution | | | Maintenance condition for amphiphilic substance solution | | Mixed solution | |
|---|---|---|---|---|---|---|---|---|---|---|
| | two-dimensional material (1.5 g) | solvent (volume) | temperature (° C.) | amphiphilic substance (mole number or weight) | solvent (volume) | heating temperature | temperature (° C.) | maintenance time (hr) | temperature (° C.) | maintenance time (hr) |
| Preparation Example 18 | boron nitride | ODCB (50 ml) | R.T. | bile acid derivative (Formula 4) (0.02 mmol) | ODCB (20 ml) | 60 | — | — | R.T. | 24 |
| Preparation Example 19 | boron nitride | ODCB (50 ml) | R.T. | bile acid derivative (Formula4) (0.02 mmol) | ODCB (10 ml) | 60 | R.T. | 24 | R.T. | 24 |
| Preparation Example 20 | boron nitride | acetone (60 ml) | R.T. | N-hexadecyltrimethyl-ammonium salt (0.01 g) | acetone (10 ml) | 15° C. | 0° C. | 1 | 20° C. | 24 |
| Preparation Example 21 | boron nitride | ODCB (20 ml) | 55° C. | benzalkonium chloride (0.01 g) | ODCB (10 ml) | 130° C. | 0° C. | 3 | 300° C. | 24 |
| Preparation Example 22 | boron nitride | toluene (15 ml) | 65° C. | bile acid derivative (Formula 7) (0.005 g) | toluene (10 ml) | 100° C. | — | — | R.T. | 11 |
| Preparation Example 23 | boron nitride | Isopropyl alcohol (150 ml) | 30° C. | bile acid derivative (Formula 8) (0.05 g) | Isopropyl alcohol (100 ml) | 60° C. | R.T. | 24 | 100° C. | 24 |
| Preparation Example 24 | boron nitride | benzene (5 ml) | 45° C. | sodium dodecyl sulfate (0.001 g) | benzene (1 ml) | 100° C. | 4° C. | 1 | 5° C. | 4 |
| Preparation Example 25 | boron nitride | tetrahydrofuran (5 ml) | R.T. | sodium larureth sulfate (0.001 g) | tetrahydrofuran (1 ml) | 60° C. | 0° C. | 0.5 | 250° C. | 0.1 |
| Preparation Example 26 | boron nitride | ODCB (5 ml) | R.T. | cetylpyridyl chloride (0.001 g) | ODCB (1 ml) | 180° C. | −10° C. | 1 | R.T. | 12 |
| Preparation Example 27 | boron nitride | carbon tetrachloride (5 ml) | 30° C. | alpha-tocopherol (0.001 g) | carbon tetrachloried (1 ml) | 30° C. | 4° C. | 1 | 60° C. | 3 |
| Preparation Example 28 | boron nitride | ODCB (5 ml) | 60° C. | sodium taurocholate (0.001 g) | ODCB (1 ml) | 120° C. | — | — | 180° C. | 5 |
| Preparation Example 29 | boron nitride | chloroform (50 ml) | 50° C. | M13 (0.03 g) | chloroform (20 ml) | 50° C. | −196° C. | 4 | 10° C. | 7 |

TABLE 3-continued

| | Two-dimensional material dispersion | | | Amphiphilic substance solution | | | Maintenance condition for amphiphilic substance solution | | Mixed solution | |
|---|---|---|---|---|---|---|---|---|---|---|
| Preparation Example | two-dimensional material (1.5 g) | solvent (volume) | temperature (° C.) | amphiphilic substance (mole number or weight) | solvent (volume) | heating temperature | temperature (° C.) | maintenance time (hr) | temperature (° C.) | maintenance time (hr) |
| Preparation Example 30 | boron nitride | acetic acid (50 ml) | 40° C. | fd (0.01 g) | acetic acid (20 ml) | 40° C. | −20° C. | 0.1 | R.T. | 10 |
| Preparation Example 31 | boron nitride | ODCB (10 ml) | R.T. | T2 (0.001 g) | ODCB (1 ml) | 150° C. | −10° C. | 12 | 200° C. | 24 |
| Preparation Example 32 | boron nitride | water (10 ml) | R.T. | MS2 (0.001 g) | water (1 ml) | 100° C. | 0° C. | 3 | 300° C. | 0.5 |

TABLE 4

| | Two-dimensional material dispersion | | | Amphiphilic substance solution | | |
|---|---|---|---|---|---|---|
| Preparation Example | two-dimensional material (1.5 g) | solvent (volume) | temperature (° C.) | amphiphilic substance (mole number or weight) | solvent (volume) | heating temperature |
| Preparation Example 33 | molybdenum sulfide | methanol (15 ml) | R.T. | cetyl alcohol (0.02 g) | methanol (10 ml) | 60° C. |
| Preparation Example 34 | molybdenum sulfide | heptane (30 ml) | 60° C. | polyoxyethylene-polyoxypropylene (0.003 g) | heptane (10 ml) | 55° C. |
| Preparation Example 35 | molybdenum sulfide | carbon disulfide (30 ml) | 50° C. | lauryloyl microgol glyceride (0.007 g) | carbon disulfide (10 ml) | 120° C. |
| Preparation Example 36 | molybdenum sulfide | dichloromethane (5 ml) | 60° C. | sodium cholate hydrate (0.001 g) | dichloromethane (1 ml) | 70° C. |
| Preparation Example 37 | molybdenum sulfide | acetone (5 ml) | 65° C. | deoxycholic acid (0.001 g) | acetone (1 ml) | 70° C. |
| Preparation Example 38 | molybdenum sulfide | ODCB (5 ml) | 30° C. | bile acid derivative (Formula4) (0.02 mmol) | ODCB (1 ml) | 60° C. |
| Preparation Example 39 | molybdenum sulfide | toluene (5 ml) | 45° C. | bile acid derivative (Formula5) (0.02 mmol) | toluene (1 ml) | 120° C. |
| Preparation Example 40 | molybdenum sulfide | Isopropyl alcohol (15 ml) | 60° C. | bile acid derivative (Formula6) (0.005 g) | Isopropyl alcohol (1 ml) | 70° C. |
| Preparation Example 41 | molybdenum sulfide | benzene (15 ml) | R.T. | bile acid derivative (Formula7) (0.004 g) | benzene (5 ml) | 100° C. |
| Preparation Example 42 | molybdenum sulfide | tetrahydrofuran (5 ml) | R.T. | bile acid derivative (Formula8) (0.005 g) | tetrahydrofuran (1 ml) | 60° C. |
| Preparation Example 43 | molybdenum sulfide | ODCB (5 ml) | 65° C. | T2 (0.001 g) | ODCB (1 ml) | 180° C. |
| Preparation Example 44 | molybdenum sulfide | carbon tetrachloride (5 ml) | 30° C. | T4 (0.005 g) | carbon tetrachloride (1 ml) | 30° C. |
| Preparation Example 45 | molybdenum sulfide | ODCB (15 ml) | 45° C. | M13 (0.001 g) | ODCB (10 ml) | 120° C. |
| Preparation Example 46 | molybdenum sulfide | chloroform (50 ml) | R.T. | fd (0.006 g) | chloroform (10 ml) | 50° C. |
| Preparation Example 47 | molybdenum sulfide | acetic acid (50 ml) | R.T. | P22 (0.008 g) | acetic acid (10 ml) | 60° C. |

TABLE 4-continued

| Preparation Example | | | | | | | |
|---|---|---|---|---|---|---|---|
| Preparation Example 48 | molybdenum sulfide | dichloromethane (15 ml) | R.T. | fd/ bile acid derivative (Formula7) (0.05 g) | | dichloromethane (10 ml) | 55° C. |
| Preparation Example 49 | molybdenum sulfide | ODCB (5 ml) | R.T. | P22/ cetyl alcohol (0.005 g) | | ODCB (1 ml) | 120° C. |
| Preparation Example 50 | molybdenum sulfide | chloroform (5 ml) | R.T. | Al(OH)$_3$/ N-hexadecyltrimethylammonium salt (0.002 g) | | chloroform (1 ml) | 40° C. |
| Preparation Example 51 | molybdenum sulfide | acetic acid (5 ml) | 40° C. | SiO$_2$/ sodium dodecyl sulfate (0.007 g) | | acetic acid (1 ml) | 70° C. |

| | Maintenance condition for amphiphilic substance solution | | Mixed solution | |
|---|---|---|---|---|
| Preparation Example | temperature (° C.) | maintenance time (hr) | temperature (° C.) | maintenance time (hr) |
| Preparation Example 33 | — | — | 180° C. | 10 |
| Preparation Example 34 | 0° C. | 1 | 10° C. | 24 |
| Preparation Example 35 | 0° C. | 3 | R.T. | 11 |
| Preparation Example 36 | — | — | 200° C. | 24 |
| Preparation Example 37 | — | — | 300° C. | 4 |
| Preparation Example 38 | 4° C. | 10 | R.T. | 0.1 |
| Preparation Example 39 | 0° C. | 24 | 100° C. | 12 |
| Preparation Example 40 | −10° C. | 11 | R.T. | 3 |
| Preparation Example 41 | 4° C. | 24 | 250° C. | 5 |
| Preparation Example 42 | R.T. | 24 | R.T. | 7 |
| Preparation Example 43 | R.T. | 0.5 | 60° C. | 10 |
| Preparation Example 44 | 18° C. | 24 | 180° C. | 24 |
| Preparation Example 45 | 4° C. | 12 | 10° C. | 0.5 |
| Preparation Example 46 | — | — | R.T. | 2 |
| Preparation Example 47 | — | — | 200° C. | 2 |
| Preparation Example 48 | — | — | R.T. | 24 |
| Preparation Example 49 | — | — | 100° C. | 11 |

TABLE 4-continued

| | | | | |
|---|---|---|---|---|
| Preparation Example 50 | R.T. | 18 | R.T. | 0.1 |
| Preparation Example 51 | −60° C. | 2 | 250° C. | 0.5 |

TABLE 5

| Preparation Example | Two-dimensional material dispersion | | | Amphiphilic substance solution | | | Maintenance condition for amphiphilic substance solution | | Mixed solution | |
|---|---|---|---|---|---|---|---|---|---|---|
| | two-dimensional material (1.5 g) | solvent (volume) | temperature (° C.) | amphiphilic substance (mole number or weight) | solvent (volume) | heating temperature | temperature (° C.) | maintenance time (hr) | temperature (° C.) | maintenance time (hr) |
| Preparation Example 52 | graphene/boron carbon nitride (BCN) | carbon tetrachloride (15 ml) | 70° C. | sodium laureth sulfate (0.001 g) | carbon tetrachloride (10 ml) | 30° C. | 0° C. | 1 | 10° C. | 24 |
| Preparation Example 53 | graphene/boron carbon nitride (BCN) | ODCB (15 ml) | 55° C. | cetylpyridyl chloride (0.02 mmol) | ODCB (10 ml) | 180° C. | 0° C. | 3 | R.T. | 11 |
| Preparation Example 54 | graphene/boron carbon nitride (BCN) | chloroform (20 ml) | R.T. | alpha-tocopherol (0.02 g) | chloroform (1 ml) | 40° C. | −55° C. | 0.5 | 200° C. | 24 |
| Preparation Example 55 | graphene/boron carbon nitride (BCN) | acetic acid (20 ml) | R.T. | sodium taurocholate (0.002 g) | acetic acid (1 ml) | 70° C. | −25° C. | 24 | 300° C. | 4 |
| Preparation Example 56 | graphene/boron carbon nitride (BCN) | ODCB (500 ml) | 40° C. | M13 (0.1 g) | ODCB (100 ml) | 180° C. | — | — | R.T. | 0.1 |
| Preparation Example 57 | graphene/boron carbon nitride (BCN) | water (500 ml) | 55° C. | fd (0.05 g) | water (100 ml) | 100° C. | — | — | 100° C. | 12 |
| Preparation Example 58 | graphene/boron carbon nitride (BCN) | methanol (100 ml) | 40° C. | T2 (0.05 g) | methanol (100 ml) | 65° C. | R.T. | 12 | R.T. | 3 |
| Preparation Example 59 | graphene/boron carbon nitride (BCN) | heptane (500 ml) | 55° C. | MS2 (0.03 g) | heptane (50 ml) | 60° C. | 10° C. | 5 | 250° C. | 5 |
| Preparation Example 60 | graphene/molybdenum sulfide | ODCB (5 ml) | R.T. | bile acid derivative (Formula 5) (0.02 mmol) | ODCB (1 ml) | 120° C. | R.T. | 24 | 60° C. | 10 |
| Preparation Example 61 | graphene/molybdenum sulfide | carbon tetrachloride (5 ml) | R.T. | bile acid derivative (Formula 6) (0.02 mmol) | carbon tetrachloride (1 ml) | 30° C. | — | — | 180° C. | 24 |
| Preparation Example 62 | graphene/molybdenum sulfide | ODCB (20 ml) | 40° C. | bile acid derivative (Formula 7) (0.02 mmol) | ODCB (10 ml) | 200° C. | — | — | R.T. | 0.5 |
| Preparation Example 63 | graphene/molybdenum sulfide | chloroform (25 ml) | 70° C. | bile acid derivative (Formula 8) (0.02 g) | chloroform (10 ml) | 40° C. | 0° C. | 1 | 100° C. | 2 |
| Preparation Example 64 | graphene/molybdenum sulfide | acetic acid (50 ml) | R.T. | sodium dodecyl sulfate (0.05 g) | acetic acid (10 ml) | 70° C. | 0° C. | 3 | R.T. | 2 |
| Preparation Example 65 | graphene/molybdenum sulfide | ODCB (5 ml) | R.T. | lauryloyl microgol glyceride (0.001 g) | ODCB (1 ml) | 120° C. | — | — | 250° C. | 5 |

TABLE 6

| Preparation Example | Two-dimensional material dispersion | | | Amphiphilic substance solution | | | Maintenance condition for amphiphilic substance solution | | Mixed solution | |
|---|---|---|---|---|---|---|---|---|---|---|
| | two-dimensional material (1.5 g) | solvent (volume) | temperature (° C.) | amphiphilic substance (mole number or weight) | solvent (volume) | heating temperature (° C.) | temperature (° C.) | maintenance time (hr) | temperature (° C.) | maintenance time (hr) |
| Preparation Example 66 | graphene | ODCB (5 ml) | R.T. | bile acid derivative (Formula 13) (0.02 mmol) | ODCB (1 ml) | 120° C. | R.T. | 24 | 60° C. | 10 |
| Preparation Example 67 | graphene | carbon tetrachloride (5 ml) | R.T. | bile acid derivative (Formula 14) (0.02 mmol) | carbon tetrachloride (1 ml) | 30° C. | — | — | 180° C. | 24 |
| Preparation Example 68 | graphene | ODCB (20 ml) | 40° C. | bile acid derivative (Formula 15) (0.02 mmol) | ODCB (10 ml) | 200° C. | — | — | R.T. | 0.5 |
| Preparation Example 69 | boron nitride | chloroform (25 ml) | 70° C. | bile acid derivative (Formula 16) (0.02 g) | chloroform (10 ml) | 40° C. | 0° C. | 1 | 100° C. | 2 |
| Preparation Example 70 | boron nitride | acetic acid (50 ml) | R.T. | bile acid derivative (Formula 17) (0.02 mmol) | acetic acid (10 ml) | 70° C. | 0° C. | 3 | R.T. | 2 |
| Preparation Example 71 | molybdenum sulfide | ODCB (5 ml) | 60° C. | bile acid derivative (Formula 18) (0.02 mmol) | ODCB (1 ml) | 120° C. | — | — | 250° C. | 5 |
| Preparation Example 72 | molybdenum sulfide | ODCB (5 ml) | R.T. | bile acid derivative (Formula 19) (0.02 mmol) | ODCB (1 ml) | 120° C. | — | — | 250° C. | 5 |
| Preparation Example 73 | molybdenum sulfide | ODCB (5 ml) | 60° C. | bile acid derivative (Formula 20) (0.02 mmol) | ODCB (1 ml) | 40° C. | 0° C. | 1 | 100° C. | 2 |

ODCB: Ortho-DichloroBenzene

Preparation Examples 74 to 91

Any one of the two-dimensional material scroll composites prepared in Preparation Examples 1, 2, 3, 9, 10, 18, 19, 26, 27, 28, 39, 40, 41, 42, 52, 53, 61, and 62 was added to a solvent shown in Table 7, and maintained at a temperature shown in Table 7 for a treatment time shown in Table 7. As a result, the amphiphilic substance contained in the scroll composite was removed, and thus only a hollow scroll remained.

TABLE 7

| Preparation Example | Scroll composite Preparation Example | Two-dimensional material | Amphiphilic substance | Solvent | Thermal treatment | Removal or not |
|---|---|---|---|---|---|---|
| Preparation Example 74 | Preparation Example 1 | graphene | bile acid derivative (Formula 4) | methanol | 200° C. | ○ |
| Preparation Example 75 | Preparation Example 2 | graphene | bile acid derivative (Formula 4) | methanol | 200° C. | ○ |
| Preparation Example 76 | Preparation Example 3 | graphene | bile acid derivative (Formula 5) | ethanol | 300° C. | ○ |
| Preparation Example 77 | Preparation Example 9 | graphene | sodium chlorate hydrate | propanol | 450° C. | ○ |
| Preparation Example 78 | Preparation Example 10 | graphene | deoxycholic acid | tetrahydrofuran | 400° C. | ○ |
| Preparation Example 79 | Preparation Example 18 | boron nitride | bile acid derivative (Formula 4) | methanol | 400° C. | ○ |

TABLE 7-continued

| Preparation Example | Scroll composite Preparation Example | Two-dimensional material | Amphiphilic substance | Solvent | Thermal treatment | Removal or not |
|---|---|---|---|---|---|---|
| Preparation Example 80 | Preparation Example 19 | boron nitride | bile acid derivative (Formula 4) | methanol | 300° C. | ○ |
| Preparation Example 81 | Preparation Example 26 | boron nitride | cetylpyridyl chloride | carbon tetrachloride | 150° C. | ○ |
| Preparation Example 82 | Preparation Example 27 | boron nitride | synthetic vitamin E derivative | ODCB | 500° C. | ○ |
| Preparation Example 83 | Preparation Example 28 | boron nitride | sodium taurocholate | carbon tetrachloride | 200° C. | ○ |
| Preparation Example 84 | Preparation Example 39 | molybdenum sulfide | bile acid derivative (Formula5) | ODCB | 450° C. | ○ |
| Preparation Example 85 | Preparation Example 40 | molybdenum sulfide | bile acid derivative (Formula6) | methanol | 600° C. | ○ |
| Preparation Example 86 | Preparation Example 41 | molybdenum sulfide | bile acid derivative (Formula 7) | ethanol | 800° C. | ○ |
| Preparation Example 87 | Preparation Example 42 | molybdenum sulfide | bile acid derivative (Formula 8) | propanol | 700° C. | ○ |
| Preparation Example 88 | Preparation Example 52 | graphene/boron carbon nitride (BCN) | sodium laureth sulfate | carbon tetrachloride | 300° C. | ○ |
| Preparation Example 89 | Preparation Example 53 | graphene/boron carbon nitride (BCN) | cetylpyridyl chloride | ODCB | 600° C. | ○ |
| Preparation Example 90 | Preparation Example 61 | graphene/molybdenum sulfide | bile acid derivative Formula6 | carbon tetrachloride | 350° C. | ○ |
| Preparation Example 91 | Preparation Example 62 | graphene/molybdenum sulfide | bile acid derivative Formula 7 | ODCB | 200° C. | ○ |

FIG. 10 shows the scanning electron microscope (SEM) image (a) and the transmission electron microscope (TEM) image (b) showing the boron nitride dispersion obtained during the process of Preparation Example 18.

Referring to FIG. 10, exfoliated hexagonal-boron nitride (exfoliated h-BN) was multi-layers boron nitride in which multiple layers were stacked in parallel, and its size corresponded to several hundred nanometers.

FIG. 11 shows the image (a) of the boron nitride dispersion obtained during the process of Preparation Example 18 and the image (c) of a mixed solution of the dispersion and a bile acid derivative solution of Formula 4. While Preparation Example 18 and the image (c) use 0.02 mmol of the bile acid derivative of Formula 4, the images (b) and (d) were respectively obtained with mixed solutions of boron nitride dispersions obtained with different mole numbers, for example, 0.01 mmol and 0.1 mmol of the bile acid derivative of Formula 4 and the bile acid derivative solution of Formula 4.

Referring to FIG. 11, as the mole number of the bile acid derivative as an amphiphilic substance increases, it can be seen that the density of floating precipitates is increased, and phase separation is induced. Here, while precipitates on the bottom are coagulated h-BN and h-BN multiple layers, almost all of the floating precipitates are boron nitride scroll composite materials.

FIG. 12 shows the TEM images (a) and high resolution (HR)-TEM images (b, c, d, e, f) of the boron nitride scroll composite materials obtained in Preparation Example 18.

Referring to FIG. 12, it can be seen that the boron nitride scroll composite materials having the bile acid derivative of Formula 4 inside and formed by interactions between h-BN sheets have a tube-like shape. It can be seen that the inner diameter of the boron nitride scroll composite material is 20 to 60 nm, and the distance between planes (d-spacing) in walls of the boron nitride scroll composite material is 0.33 nm (see b). 0.33 nm corresponds to the interlayer distance of the multi-layered h-BN sheets and the BN nanotube. One boron nitride scroll that is completely rolled up is shown in the images (c) and (d), and the enlarged images of the part represented by a circle in the images (c) and (d) are shown in (e) and (0, respectively. It can be seen that the ends of the scroll in (e) and (f) are round.

FIG. 13 shows the TEM image (a) of the boron nitride dispersion obtained during the process of Preparation Example 18, and the TEM images b, c and d of boron nitride scroll composite materials.

Referring to FIG. 13, the images (b) and (c) correspond to an initial stage of scrolling h-BN, and the image (d) shows completed scrolling.

FIG. 14 shows the Raman graph of exfoliated h-BN (a) obtained during the process of Preparation Example 18 and a BN scroll composite material (b) obtained in Preparation Example 18.

Referring to FIG. 14, the exfoliated h-BN (a) shows an $E_{2g}$ phonon mode with a full width at half maximum (FWHM) of 16 cm$^{-1}$ at 1364 cm$^{-1}$, the BN scroll composite material (b) shows an $E_{2g}$ phonon mode with an FWHM of 19 cm$^{-1}$ at 1366 cm$^{-1}$. It is assumed that the increases in a blue shift (2 cm$^{-1}$) and FWHM (3 cm$^{-1}$) in the $E_{2g}$ phonon mode of the BN scroll composite material were caused by a lip-lip interaction between scrolled h-BN sheets and a morphological change of the BN scroll.

FIG. 15 shows the HR-TEM images of the BN scroll composite material (a) obtained in Preparation Example 18 and a BN scroll composite material (b) obtained in Preparation Example 19.

Referring to FIG. 15, it can be seen that, compared with the BN scroll composite material (a) obtained in Preparation Example 18, the BN scroll composite material (b) obtained in Preparation Example 19 has a larger inner diameter due to self assembly of the bile acid derivative of Formula 4. Moreover, it can be seen that, in Preparation Example 19, the bile acid derivative of Formula 4 is self-assembled, thereby forming a fiber. In Preparation Example 19, a process of forming the bile acid derivative solution at 60° C. and maintaining the solution at room temperature for 24 hours is performed, and it is assumed that, in such a process, a fiber was formed by recrystallization of the bile acid derivative. As described above, it can be seen that the inner diameter of the two-dimensional material scroll can be changed by the recrystallization of an amphiphilic substance.

FIG. 16 shows the SEM images (a, b) and TEM images (c, d) of BN scrolls obtained according to Preparation Examples 79 and 80.

Referring to FIG. 16, (c) is the TEM image of the BN scroll composite having a relatively smaller inner diameter obtained according to Preparation Example 18, washed with methanol several times in Preparation Example 79, and it can be seen that a bile acid derivative contained inside is etched only at both ends of the BN scroll composite. (d) is the TEM image of the BN scroll composite having a relatively smaller inner diameter obtained according to Preparation Example 18, precipitated in methanol and maintained for several days in Preparation Example 79, and it can be seen that a bile acid derivative contained inside is completely removed, thereby forming a hollow BN scroll. (a) and (b) are the SEM images of the BN scroll composite having a relatively larger inner diameter obtained according to Preparation Example 19, washed with methanol several times in Preparation Example 80, and it can be seen that a hollow BN scroll having a relatively larger inner diameter of approximately 125 nm is formed.

FIG. 17 shows the TGA graph (a) and TEM image (b) of boron nitride, the bile acid derivative of Formula 4, and the BN scroll composite obtained according to Preparation Example 18, obtained by thermal treatment in a nitrogen atmosphere.

Referring to FIG. 17(a), it can be seen that boron nitride is decreased a little in weight until 810° C. The bile acid derivative (LCA) of Formula 4 started to be rapidly degraded at approximately 300° C., slowly degraded between 400 and 810° C., and thus completely removed. Meanwhile, the BN scroll composite (S-BNS) prepared according to Preparation Example 18 shows a similar curve to the bile acid derivative of Formula 4, but finally, a 16.3 wt % residue was left. It is assumed that the residue was a hollow BN scroll from which a bile acid derivative contained inside was removed with heat.

Referring to FIG. 17(b), it can be seen that the sidewall of the hollow BN scroll is composed of 6 to 7 sheets.

FIG. 18 shows the SEM image of a graphene dispersion obtained during the process of Preparation Example 1.

Referring to FIG. 18, exfoliated graphene is multi-layers graphene in which multiple layers are stacked in parallel, and its size corresponded to several hundred nanometers.

FIG. 19 shows the image (A) of the graphene dispersion obtained during the process of Preparation Example 1, and the image (D) of a mixed solution of the dispersion and the bile acid derivative of Formula 4.

While Preparation Example 1 and the image (D) use 0.02 mmol of the bile acid derivative of Formula 4, the images (B), (C), and (E) were respectively obtained with mixed solutions of the solutions of the bile acid derivative of Formula 4 obtained with different mole numbers, for example, 0.001 mmol, 0.01 mmol and 0.1 mmol of the bile acid derivative of Formula 4 and the graphene dispersion.

Referring to FIG. 19, as the mole number of the bile acid derivative as the amphiphilic substance increases, it can be seen that the density of floating precipitates is increased, and phase separation is induced. Here, while precipitates on the bottom are coagulated graphene and graphene multiple layers, almost all of the floating precipitates are graphene scroll composite materials.

FIG. 20 shows the HR-TEM images of graphene scroll composite materials obtained in Preparation Example 1.

Referring to FIG. 20, it can be seen that the graphene scroll composite materials having the bile acid derivative of Formula 4 inside and formed by interactions between graphene sheets have a tube-like shape. It can be seen that the graphene scroll composite material has an inner diameter of 12 to 20 am, has a black inside since an amphiphilic substance is added into the graphene scroll composite material, and has a d-spacing in graphene walls of 0.33 nm.

FIG. 21 shows the Raman graph of an exfoliated graphene (G5 dispersion) obtained during the process of Preparation Example 2, graphene powder and a graphene scroll composite material (M-GNSs) obtained in Preparation Example 2.

Referring to FIG. 21, the exfoliated graphene shows G and D phonon modes at 1576 $cm^{-1}$ and 2677 $cm^{-1}$, the graphene powder shows the G and D phonon modes at 1570 $cm^{-1}$ and 2673 $cm^{-1}$, and the graphene scroll composite material shows G and D phonon modes at 1564 $cm^{-1}$ and 2698 $cm^{-1}$.

It is assumed that such G and D phonon shifts of the graphene scroll composite material were caused by the π-π interactions (pi-pi interactions) between scrolled graphene sheets and a morphological change of the graphene scroll.

FIG. 22 shows the SEM images of graphene scroll composite materials obtained during the process of Preparation Example 2.

Referring to FIG. 22, it is confirmed that the inner diameter of the graphene scroll composite material is 250 nm, and an amphiphilic substance inside the graphene scroll composite material forms a fiber.

FIG. 23 shows the HR-TEM images (A, B, C) of the graphene scroll obtained according to Preparation Example 74, and the SEM images (D, E, F) of the graphene scroll obtained according to Preparation Example 75.

Referring to FIG. 23, (A) and (B) are the HR-TEM images of the graphene scroll composites having a relatively smaller inner diameter obtained according to Preparation Example 1 of Preparation Example 74, washed with methanol several times, and it can be seen that an internal bile acid derivative is etched at both ends of the graphene scroll composite. (C) is the HR-TEM image of the graphene scroll composite having a relatively smaller inner diameter obtained according to Preparation Example 1 in Preparation Example 74, precipitated in methanol and then maintained for several days, and it can be seen that the internal bile acid derivative is completely removed, and thereby forming a hollow graphene scroll having an inner diameter of approximately 5 nm. (D), (E) and (F) are the SEM images of the graphene scroll composites having a relatively larger inner diameter obtained according to Preparation Example 2 in Preparation Example 75, washed with methanol several times, and it can be seen that a hollow graphene scroll is formed to have a relatively larger inner diameter of approximately 300 nm.

FIG. 24 shows the TGA graph (a) and TEM image (b) of graphite, the bile acid derivative of Formula 4, and the graphene scroll composite obtained according to Preparation Example 1, obtained by thermal treatment in a nitrogen atmosphere.

Referring to FIG. 24(a), it can be seen that graphite is decreased only a little in weight until 810° C. The bile acid derivative of Formula 4 started drastic deterioration at approximately 300° C., was gradually degraded between 400 to 810° C., and then completely removed. The graphene scroll composite prepared according to Preparation Example 1 showing a similar curve to the bile acid derivative of Formula 4, but finally, a 24.5 wt % residue was left. It was assumed that such a residue was a hollow graphene scroll from which an internal bile acid derivative was removed by heat.

Referring to FIG. 24(b), it can be seen that the sidewall of the hollow graphene scroll is composed of 10 to 11 sheets.

FIG. 25 is the SEM image of the amphiphilic substance solution obtained during the process of Preparation Example 11.

Referring to FIG. 25, it can be confirmed that metal particles (Ag) and an amphiphilic substance (sodium dodecyl sulfate) are sufficiently mixed. This indicates that a two-dimensional material scroll composite can be formed by depositing the metal particles and the amphiphilic substance inside a two-dimensional material scroll through self assembly.

As described above, the present invention has been described with reference to exemplary specific preparation examples. However, the scope of the present invention encompasses all of simple modifications or alternations of the present invention, and therefore will be specified by the accompanying claims.

The invention claimed is:

1. A two-dimensional material scroll, which has a sheet of two-dimensional material which is rolled up to form the scroll, the rolled-up sheet has a first edge exposed inside the scroll and a second edge opposite to the first edge is exposed outside of the scroll, wherein interactions are between adjacent in-plane regions of the two-dimensional material sheet, and open ends,
   wherein the two-dimensional material is a single substance selected from the group consisting of boron nitride, boron carbon nitride (BCN), tungsten oxide ($WO_3$), tungsten sulfide ($WS_2$), molybdenum sulfide ($MoS_2$), molybdenum telluride ($MoTe_2$), and manganese oxide ($MnO_2$), or a composite substance including a stack of two or more thereof, and
   wherein a diameter inside the scroll is between 20 nm to 300 nm.

2. The scroll of claim 1, wherein the two-dimensional material scroll is a hollow scroll including an empty inside.

3. A scroll composite, comprising:
   the two-dimensional material scroll with open ends of claim 1; and
   amphiphilic substance disposed inside the scroll.

4. The composite of claim 3, wherein the amphiphilic substance is a surfactant, a bile acid, a bile acid salt, a hydrate of a bile acid salt, a bile acid ester, a bile acid derivative, or a bacteriophage.

5. The composite of claim 4, wherein the surfactant includes one or more compounds selected from the group consisting of sodium dodecyl sulfate (SDS), ammonium lauryl sulfate, sodium laureth sulfate, alkyl benzene sulfonate, cetyl trimethylammonium bromide (CTAB), hexadecyl trimethyl ammonium bromide, an alkyltrimethylammonium salt, cetylpyridinium chloride (CPCI), polyethoxylated tallow amine (POEA), benzalkonium chloride (BAC), benzethonium chloride (BZT), dodecyl betaine, dodecyl dimethylamine oxide, cocamidopropyl betaine, alkyl poly(ethylene oxide), a poloxamer, a poloxamine, alkyl polyglucoside, cetyl alcohol, sodium deoxycholate, cocamide MEA, cocamide DEA, sorbitan ester, polyoxyethylene sorbitan fatty acid ester, sucrose fatty acid ester, polyethyelene glycol hydroxystearate, polyoxyethylene glycolated natural or hydrogenated castor oil, a polyoxyethylene-polyoxypropylene copolymer, a synthetic vitamin E derivative, polyoxyethylene alkyl ester, fatty acid microgol glyceride, polyglyceryl fatty acid ester, and a silicone-based surfactant.

6. The composite of claim 4, wherein the bile acid is represented by Formula 1 as follows:

[Formula 1]

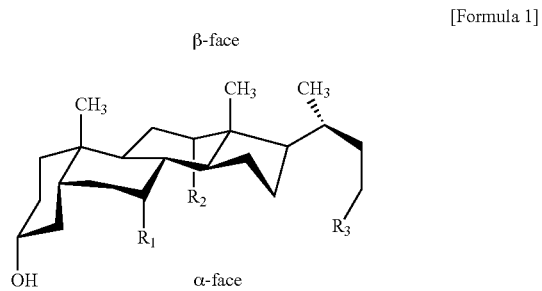

where $R_1$ and $R_2$ are each independently —H or —OH, $R_3$ is —(CONH—$(CH_2)_{n1})_{n2}$—$Y_1$, n1 is 1 or 2, n2 is 1 or 0, and $Y_1$ is —COOH or —$SO_3H$.

7. The composite of claim 6, wherein the bile acid is at least one selected from the group consisting of cholic acid, chenodeoxycholic acid, deoxycholic acid, lithocholic acid, glycocholic acid, taurocholic acid, glycochenodeoxycholic acid, taurochenodeoxycholic acid, glycodeoxycholic acid, taurodeoxycholic acid, glycolithocholic acid, and taurolithocholic acid.

8. The composite of claim 6, wherein the bile acid salt is sodium glycochenodeoxycholate, sodium taurochenodeoxycholate, sodium taurocholate, sodium dehydrocholate, or sodium deoxycholate.

9. The composite of claim 6, wherein the hydrate of the bile acid salt is sodium taurocholate hydrate or sodium cholate hydrate.

10. The composite of claim 4, wherein the bile acid derivative is represented by Formula 2 below:

[Formula 2]

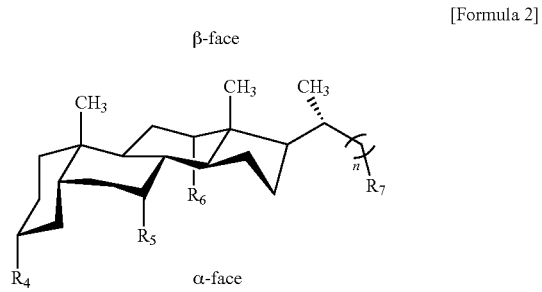

where n is 0, 1 or 2, and $R_4$ to $R_7$ are each independently a group represented by Formula 3,

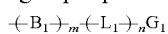 [Formula 3]

where $B_1$ is one group selected from the group consisting of

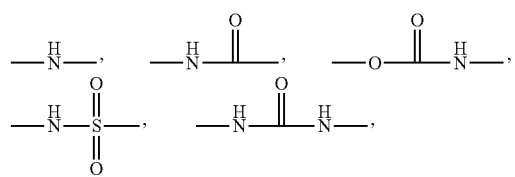

-continued

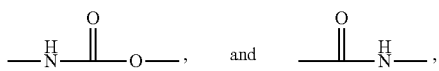

$L_1$ is a linker of —$W_1$—, -$Q_1$-, -$Q_2$-$W_2$—, —$W_2$-$Q_1$-$W_3$—, or —$W_4$-$Q_2$-$W_5$-$Q_3$-$Q_6$-, $W_1$, $W_2$, $W_3$, $W_4$, $W_5$, and $W_6$ are each independently

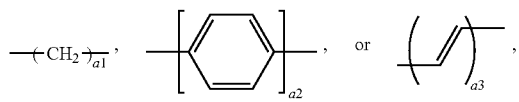

$a_1$ to $a_3$ are each an integer of 1 to 4, $Q_1$, $Q_2$, $Q_3$, $Q_4$, $Q_5$, and $Q_6$ are each independently

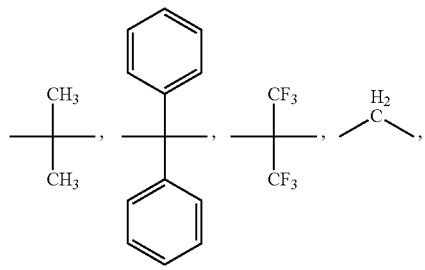

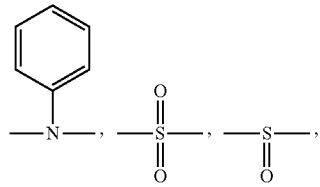

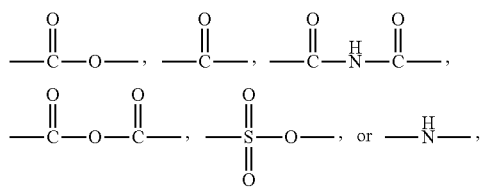

$G_1$ is a group represented by

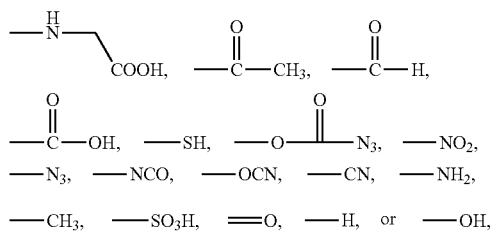

and m is 0 or 1, and n is 0 or 1.

11. The composite of claim 10, wherein the bile acid derivative is any one of Formulas 4 to 20:

[Formula 4]

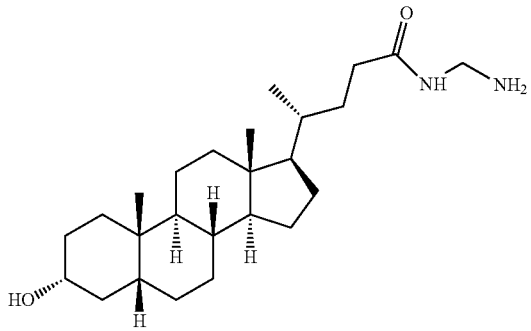

(R)-N-(aminomethyl)-4-((3R,5R,8R,9S,10S,13R,14S,17R)-3-hydroxy-10,13-dimethylhexadecahydro-1H-cyclopenta[a]phenanthren-17-yl)pentanamide

[Formula 5]

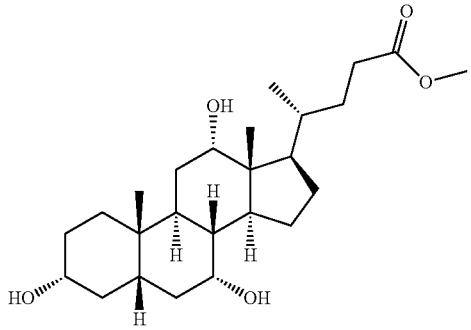

(R)-methyl-4-((3R,5S,7R,8R,9S,10S,12S,13R,14S,17R)-3,7,12-trihydroxy-10,13-dimethylhexadecahydro-1H-cyclopenta[a]phenanthren-17-yl)pentanoate

[Formula 6]

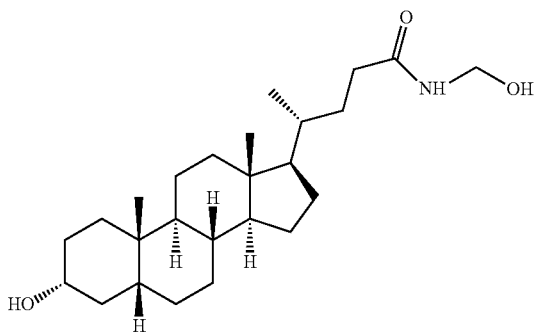

(R)-4-((3R,5R,8R,9S,10S,13R,14S,17R)-3-hydroxy-10,13-dimethylhexadecahydro-1H-cyclopenta[a]phenanthren-17-yl)-N-(hydroxymethyl)pentanamide

[Formula 7]

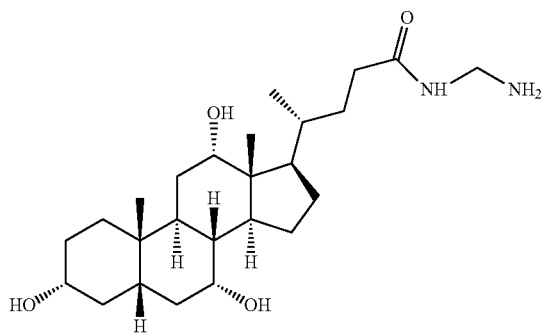

(R)-N-(aminomethyl)-4-((3R,5S,7R,8R,9S,10S,12S,13R,14S,17R)-3,7,12-trihydroxy-10,13-dimethylhexadecahydro-1H-cyclopenta[a]phenanthren-17-yl)pentanamide

[Formula 8]

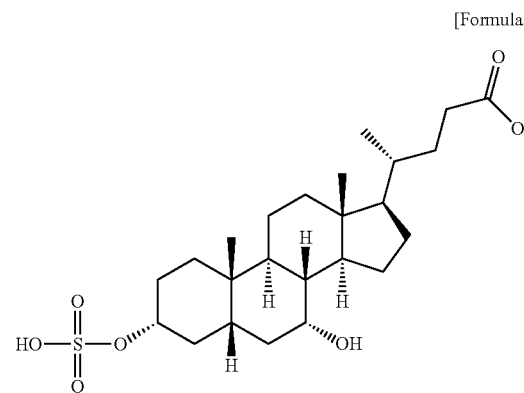

(R)-4-((3R,5R,7R,8R,9S,10S,13R,14S,17R)-7-hydroxy-10,13-dimethyl-3-(sulfooxy)hexadecahydro-1H-cyclopenta[a]phenanthren-17-yl)pentanoic acid

[Formula 9]

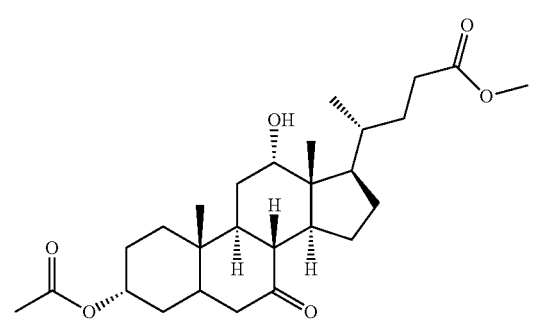

5R-cholanic acid-3α,12α-diol 3-acetate methyl ester

[Formula 10]

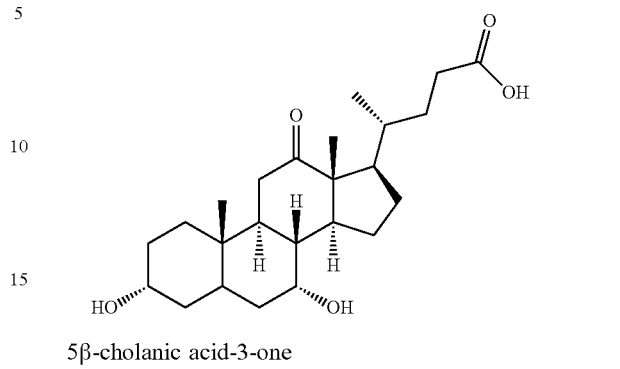

5β-cholanic acid-3-one

[Formula 11]

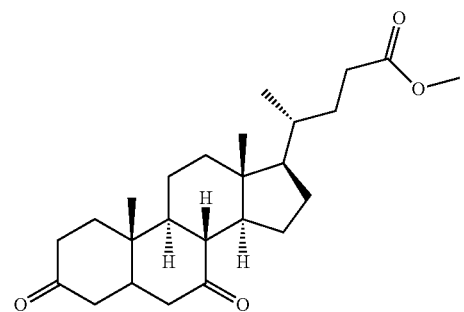

5β-cholanic acid 3,7-dione methyl ester

[Formula 12]

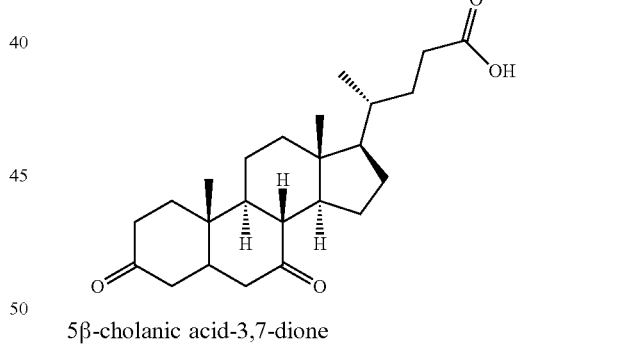

5β-cholanic acid-3,7-dione

[Formula 13]

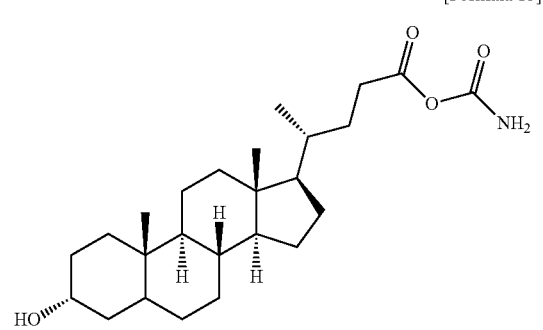

Carbamic(4R)-4-((3R,8R,9S,10S,13R,14S,17R)-3-hydroxy-10,13-dimethylhexadecahydro-1H-cyclopenta[a]phenanthren-17-yl)pentanoic anhydride

[Formula 14]

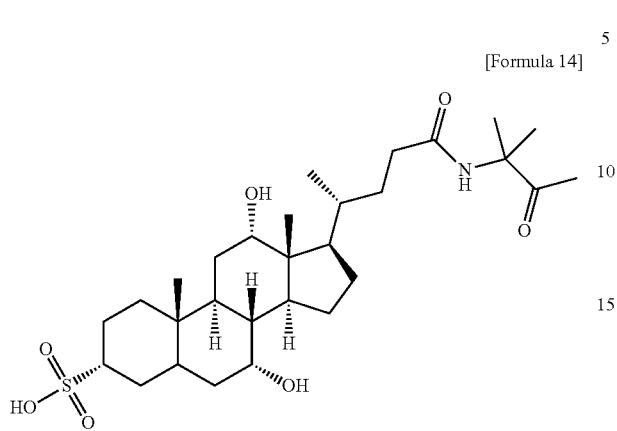

3R,7R,8R,9S,10S,12S,13R,14S,17R)-7,12-dihydroxy-10,13-dimethyl-17-((R)-5-((2-methyl-3-oxobutan-2-yl)amino)-5-oxopentan-2-yl)hexadecahydro-1H-cyclopenta[a]phenanthrene-3-sulfonic acid

[Formula 15]

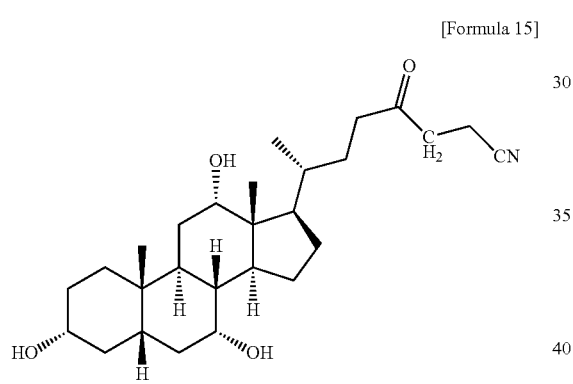

R)-4-oxo-7-((3R,5S,7R,8R,9S,10S,12S,13R,14S,17R)-3,7,12-trihydroxy-10,13-dimethylhexadecahydro-1H-cyclopenta[a]phenanthren-17-yl)octanenitrile

[Formula 16]

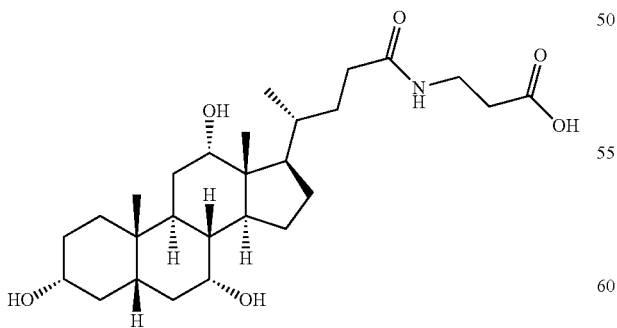

3-((R)-4-((3R,5S,7R,8R,9S,10S,12S,13R,14S,17R)-3,7,12-trihydroxy-10,13-dimethylhexadecahydro-1H-cyclopenta[a]phenanthren-17-yl)pentanamido)propanoic acid

[Formula 17]

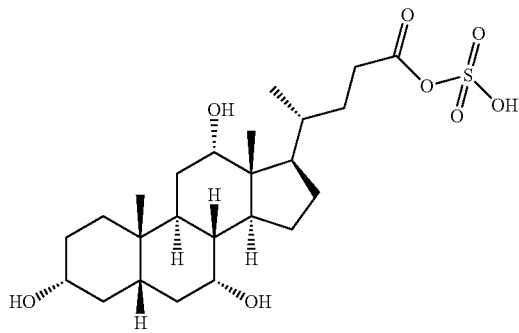

(R)-4-((3R,5S,7R,8R,9S,10S,12S,13R,14S,17R)-3,7,12-trihydroxy-10,13-dimethylhexadecahydro-1H-cyclopenta[a]phenanthren-17-yl)pentanoic sulfuric anhydride

[Formula 18]

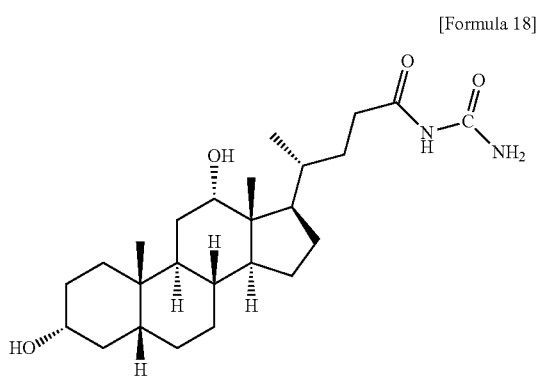

(R)-N-carbamoyl-4-((3R,5R,8R,9S,10S,12S,13R,14S,17R)-3,12-dihydroxy-10,13-dimethylhexadecahydro-1H-cyclopenta[a]phenanthren-17-yl)pentanamide

[Formula 19]

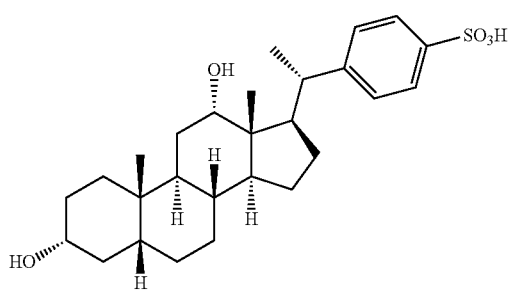

4-((S)-1-((3R,5R,8R,9S,10S,12S,13S,14S,17R)-3,12-dihydroxy-10,13-dimethylhexadecahydro-1H-cyclopenta[a]phenanthren-17-yl)ethyl)benzenesulfonic acid

[Formula 20]

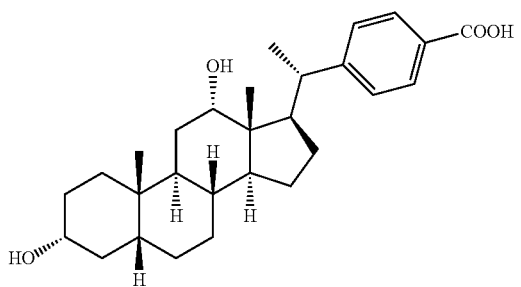

4-((S)-1-((3R,5R,8R,9S,10S,12S,13S,14S,17R)-3,12-dihydroxy-10,13-dimethylhexadecahydro-1H-cyclopenta[a]phenanthren-17-yl)ethyl)benzoic acid.

12. The composite of claim 4, wherein the bacteriophage is a filamentous bacteriophage.

13. The composite of claim 12, wherein the bacteriophage is at least one selected from the group consisting of T1, T2, T3, T4, T5, T6, T7, M13, MS2, fd, f1 and P22.

14. The composite of claim 3, wherein the amphiphilic substance is formed in a self assembly.

15. The composite of claim 14, wherein hydrophilic portions of the amphiphilic substance are exposed at the exterior of the self assembly.

16. The composite of claim 14, wherein the self assembly has a spherical, rod-shaped or fiber-shaped structure.

17. The composite of claim 14, wherein the self assembly of the amphiphilic substance includes a core particle and one or more shells including the amphiphilic substance self-assembled on the core particle.

18. The composite of claim 17, wherein hydrophilic portions of the amphiphilic substance are exposed at the exterior of the self assembly of the amphiphilic substance.

19. The composite of claim 17, wherein the core particle is spherical or rod-shaped.

20. The composite of claim 17, wherein the core particle is a metal particle, a metal oxide particle, or a bacteriophage.

21. A method for preparing a two-dimensional material scroll, comprising:
providing a sheet of two-dimensional material; and
scrolling the sheet of two-dimensional material by providing an amphiphilic substance having a hydrophilic portion and a hydrophobic portion onto the sheet of two-dimensional material to form a scroll composite of claim 3.

22. The method of claim 21, wherein the two-dimensional material is provided in the form of a two-dimensional material dispersion dispersed in a solvent.

23. The method of claim 22, wherein the providing of the amphiphilic substance includes mixing the two-dimensional material dispersion with an amphiphilic substance solution prepared by dissolving the amphiphilic substance in a solvent.

24. The method of claim 23, further comprising:
before mixing the amphiphilic substance solution with the two-dimensional material dispersion, heating the amphiphilic substance solution.

25. The method of claim 23, further comprising:
before mixing the heated amphiphilic substance solution with the two-dimensional material dispersion, cooling the heated amphiphilic substance solution.

26. The method of claim 23, wherein the amphiphilic substance solution includes a core particle.

27. The method of claim 21, further comprising:
forming the two-dimensional material scroll by removing at least a part of the amphiphilic substance therein by solvent treatment and/or thermal treatment.

28. The method of claim 27, wherein the solvent is a solvent for dissolving the amphiphilic substance.

29. The method of claim 27, wherein the thermal treatment is performed at 200 to 800° C.

* * * * *